(12) United States Patent
Downie

(10) Patent No.: US 9,459,191 B2
(45) Date of Patent: Oct. 4, 2016

(54) METHOD OF AND APPARATUS FOR MEASURING THE MOLECULAR WEIGHT OF A GAS

(75) Inventor: Neil Alexander Downie, Odiham (GB)

(73) Assignee: Air Products and Chemicals, Inc., Allentown, PA (US)

( * ) Notice: Subject to any disclaimer, the term of this patent is extended or adjusted under 35 U.S.C. 154(b) by 428 days.

(21) Appl. No.: 13/989,232

(22) PCT Filed: Nov. 28, 2011

(86) PCT No.: PCT/EP2011/071208
§ 371 (c)(1),
(2), (4) Date: Sep. 13, 2013

(87) PCT Pub. No.: WO2012/072596
PCT Pub. Date: Jun. 7, 2012

(65) Prior Publication Data
US 2014/0000342 A1 Jan. 2, 2014

(30) Foreign Application Priority Data
Nov. 29, 2010 (EP) .................................... 10192972

(51) Int. Cl.
*G01N 29/02* (2006.01)
*G01N 9/00* (2006.01)
*G01N 29/036* (2006.01)

(52) U.S. Cl.
CPC ............ *G01N 9/002* (2013.01); *G01N 29/036* (2013.01); *G01N 2291/021* (2013.01); *G01N 2291/02818* (2013.01)

(58) Field of Classification Search
CPC ............... G01N 9/002; G01N 29/036; G01N 2291/021; G01N 2291/02818
USPC .................................... 73/24.01; 24/522, 519
See application file for complete search history.

(56) References Cited

U.S. PATENT DOCUMENTS 3,561,832 A 2/1971 Karrer et al.
3,612,966 A 10/1971 Dybel
(Continued)

FOREIGN PATENT DOCUMENTS

CN 1240024 12/1999
CN 1287616 A 3/2001
(Continued)

OTHER PUBLICATIONS

Sell Johannes, Real-Time monitoring of a high pressure reactor using a gas density sensor.*
(Continued)

*Primary Examiner* — Eric S McCall
*Assistant Examiner* — Mohammed E Keramet-Amircola
(74) *Attorney, Agent, or Firm* — Larry S. Zelson

(57) ABSTRACT

There is provided a meter for measuring the molecular weight of a gas, the meter comprising a housing having an inlet and an interior for receiving said gas to be measured, a sensor assembly comprising a high-frequency planar piezoelectric crystal oscillator located within said housing so that, in use, the piezoelectric crystal oscillator is in contact with said gas, said sensor assembly being arranged: to drive the piezoelectric crystal oscillator such that the piezoelectric crystal oscillator resonates at a single resonant frequency; to measure said single resonant frequency of said piezoelectric crystal oscillator to determine the density of gas; and to determine from the density, determined or pre-determined pressure of the gas and determined or pre-determined temperature of the gas, the molecular weight of the gas.

19 Claims, 15 Drawing Sheets

(56) References Cited

U.S. PATENT DOCUMENTS

| | | | |
|---|---|---|---|
| 3,879,992 | A | 4/1975 | Bartera |
| 3,902,355 | A | 9/1975 | Weisser |
| 4,126,049 | A | 11/1978 | Cotter |
| 4,232,544 | A | 11/1980 | Stansfeld |
| 4,275,393 | A | 6/1981 | Johnston |
| 4,507,970 | A | 4/1985 | Dinger |
| 4,526,480 | A | 7/1985 | Ward |
| 4,644,796 | A | 2/1987 | Ward |
| 4,644,804 | A | 2/1987 | Ramm et al. |
| 4,680,970 | A | 7/1987 | Ueda et al. |
| 4,681,530 | A * | 7/1987 | Huber .................. B01F 3/026 137/100 |
| 4,713,774 | A | 12/1987 | Funk et al. |
| 4,724,707 | A | 2/1988 | Innerhofer |
| 4,734,609 | A * | 3/1988 | Jasmine ............... G01L 9/0022 310/311 |
| 4,741,213 | A | 5/1988 | Hojoh |
| 4,747,311 | A | 5/1988 | Hojoh |
| 4,938,068 | A | 7/1990 | Clements |
| 4,995,263 | A | 2/1991 | Stocker |
| 5,056,366 | A * | 10/1991 | Fersht ................. G01C 19/5607 73/504.15 |
| 5,136,885 | A | 8/1992 | Liebermann et al. |
| 5,220,836 | A | 6/1993 | Harms et al. |
| 5,235,844 | A | 8/1993 | Bonne et al. |
| 5,307,668 | A | 5/1994 | Vander Heyden |
| 5,307,683 | A | 5/1994 | Phelps et al. |
| 5,421,190 | A | 6/1995 | Brandle et al. |
| 5,471,882 | A * | 12/1995 | Wiggins ............... G01L 9/0022 73/152.52 |
| 5,659,129 | A | 8/1997 | Asoyan et al. |
| 5,900,534 | A | 5/1999 | Miller et al. |
| 5,954,089 | A | 9/1999 | Seymour |
| 5,958,787 | A * | 9/1999 | Schonfeld ............ G01N 29/022 422/82.01 |
| 6,003,543 | A | 12/1999 | Sulatisky et al. |
| 6,182,499 | B1 * | 2/2001 | McFarland ......... B01J 19/0046 422/68.1 |
| 6,230,731 | B1 | 5/2001 | Miller et al. |
| 6,266,996 | B1 | 7/2001 | Livingston |
| 6,286,361 | B1 | 9/2001 | Jones et al. |
| 6,532,822 | B1 | 3/2003 | Boyd |
| 7,444,878 | B1 | 11/2008 | Pepples |
| 7,454,952 | B2 | 11/2008 | Kita et al. |
| 2003/0053516 | A1 | 3/2003 | Atherton |
| 2006/0162725 | A1 * | 7/2006 | Downie ............... G05D 7/0635 128/203.12 |
| 2007/0068493 | A1 | 3/2007 | Pavlovsky |
| 2007/0186982 | A1 | 8/2007 | Cohen et al. |
| 2008/0184804 | A1 | 8/2008 | Leverrier et al. |
| 2009/0151461 | A1 | 6/2009 | Ishii |
| 2010/0107735 | A1 | 5/2010 | Pavlovsky |
| 2010/0132471 | A1 | 6/2010 | Hedtke et al. |
| 2010/0269365 | A1 | 10/2010 | Miller et al. |
| 2011/0126930 | A1 | 6/2011 | Hayashi et al. |
| 2012/0000559 | A1 | 1/2012 | Mussot |
| 2012/0256086 | A1 | 10/2012 | Husebo et al. |
| 2013/0042698 | A1 | 2/2013 | Mayr et al. |

FOREIGN PATENT DOCUMENTS

| | | | |
|---|---|---|---|
| CN | 1768312 | A | 5/2006 |
| CN | 101708437 | A | 5/2010 |
| CN | 101761779 | A | 6/2010 |
| CN | 101881640 | A | 11/2010 |
| CN | 202061563 | U | 12/2011 |
| CN | 102472653 | A | 5/2012 |
| CN | 202212112 | U | 5/2012 |
| DE | 3345750 | A1 | 6/1985 |
| DE | 3641842 | A1 | 6/1988 |
| DE | 19901119 | A1 | 7/2000 |
| DE | 10232823 | A1 * | 7/2002 |
| DE | 10232823 | A1 | 11/2003 |
| DE | 102010028475 | A1 | 11/2011 |
| EP | 0101669 | A2 | 2/1984 |
| EP | 0129753 | A1 | 2/1985 |
| EP | 0273649 | A2 | 7/1988 |
| EP | 0484569 | A1 | 5/1992 |
| EP | 0582045 | B1 | 5/1993 |
| EP | 0671680 | A1 | 9/1995 |
| EP | 1930709 | A1 | 11/2008 |
| GB | 1349256 | A | 4/1974 |
| JP | 58151517 | | 8/1983 |
| JP | 6010148 | | 1/1985 |
| JP | 6434547 | | 2/1989 |
| JP | 6434547 | U | 3/1989 |
| JP | 1170824 | A | 7/1989 |
| JP | 3068828 | A | 3/1991 |
| JP | 543044 | | 2/1993 |
| JP | 543044 | U | 6/1993 |
| JP | 09155180 | A | 6/1997 |
| JP | 10010031 | | 1/1998 |
| JP | 2002122498 | A2 | 4/2002 |
| JP | 2004219386 | A | 8/2004 |
| JP | 2004286514 | A | 10/2004 |
| JP | 2005506495 | | 3/2005 |
| JP | 2005241355 | | 9/2005 |
| JP | 2006241516 | A | 9/2006 |
| JP | 2007244946 | A | 9/2007 |
| JP | 2009198472 | A2 | 9/2009 |
| JP | 2010038867 | A | 2/2010 |
| JP | 2015520853 | A | 7/2015 |
| JP | 2015526653 | A | 9/2015 |
| JP | 2015526694 | A | 9/2015 |
| JP | 2015526695 | A | 9/2015 |
| JP | 2015526773 | A | 9/2015 |
| TW | M334632 | Y | 6/2008 |
| TW | 201118290 | | 6/2011 |
| TW | 201207339 | | 2/2012 |
| WO | 9802686 | A1 | 1/1998 |
| WO | 9940553 | A1 | 8/1999 |
| WO | 2007002288 | A2 | 1/2007 |
| WO | 2007050400 | A1 | 5/2007 |
| WO | 2011039534 | A1 | 4/2011 |
| WO | 2011138147 | A1 | 10/2011 |

OTHER PUBLICATIONS

Johannes K Sell et al, Real-time monitoring of a high pressure reactor using a gas density sensor, Sensors and Actuators A 162, 2010, pp. 215-219.

J.K. Sell et al, Real-time monitoring of a high pressure reactor using a gas density sensor, Sensors and Actuators, A: Physical, Aug. 2010, Elsevier Nld., vol. 162, NR, 2, pp. 215-219.

Zeisel, D., H. Menzi and L. Ullrich, "A precise and robust quartz sensor based on tuning fork technology for (SF6)-gas density control", Sensors and Actuators 80, pp. 233-236 (2000).

TRAFAG AG data sheets "8773 Density Sensor" (4 pp.) from 1999 (brochure date 99/04).

"User handbook GMS gas monitor system", Riset AG, Schaffhausen (Switzerland), version of Jul. 6, 2001.

Boser, Niklaus MR., Affidavit of May 10, 2009, Riset, concerning the priority of the release of the user handbook of Nov. 6, 2001.

Tietze, U. and Schenk, Ch., "Semiconductor Circuit Technology", pp. 56-59 and pp. 354-357; fourth edition, Springer-Verlag Berlin Heidelberg New York, 1978.

Kuchling H., "Physik, Formein and Gesetze" [Physics, Formulae and Laws], pp. 164-169; 7th edition, Buch-und-Zeit-Verlagsgesellschaft mbH Cologne, 1969.

Decision of the German Federal Patents Court in the matter 20 W (pat) 357/04, handed down on Oct. 12, 2009 and retrievable shortly thereafter on the internet on the home page of the German Federal Patents Court.

Density Sensor 8774 data sheet from Trafag AG, date Jan. 2006.

Suzuki et al., "GD Series Vibratory Gas Density Meters", Yokogawa Technical Report, 2000, No. 29.

(56) References Cited

OTHER PUBLICATIONS

European Patent Office, International Search Report of the International Searching Authority, mailed Jul. 18, 2013, for PCT/EP2013/060686.

European Patent Office, International Search Report of the International Searching Authority, mailed Aug. 2, 2013, for PCT/EP2013/060689.

Suzuki, Jun-ichi, "GD Series Vibratory Gas Density Meters", Yokogawa Technical Report English Edition, No. 29 (2000), pp. 23-26.

Sell, Johannes K., "Real-time monitoring of a high pressure reactor using a gas density sensor", Sensors and Actuators A: 162 (2010) 215-219.

Annex A: Documents cited in Opposition proceedings, included in letter from Beck Greener, Jun. 10, 2015 (References cited on IDS filed Nov. 13, 2015).

* cited by examiner

METHOD OF AND APPARATUS FOR MEASURING THE MOLECULAR WEIGHT OF A GAS

The present invention relates a method of, and apparatus for, measuring the molecular weight of a gas. More particularly, the present invention relates to a method of, and apparatus for, measuring the molecular weight of a gas (or the average molecular weight in the case of a mixture of gases) using a piezoelectric crystal oscillator.

The methods and apparatus described herein can be applied to systems where fluids of relatively high pressure (e.g. about 10 bar or higher) are present, such as for example, the supply of fluids in high pressure cylinders or manufacturing plants utilising high pressure fluids. The present invention relates particularly to "clean" gases, i.e. gases with little or no impurities or contaminants such as water vapour or dust.

The present invention is particularly applicable to permanent gases. Permanent gases are gases which cannot be liquefied by pressure alone, and for example can be supplied in cylinders at pressures up to 450 bar g (where bar g is a measure of the pressure in bar above atmospheric pressure). Examples are Argon and Nitrogen. However, this is not to be taken as limiting and the term gas may be considered to encompass a wider range of gases, for example, both a permanent gas and a vapour of a liquefied gas.

Vapours of liquefied gases are present above the liquid in a compressed gas cylinder. Gases which liquefy under pressure as they are compressed for filling into a cylinder are not permanent gases and are more accurately described as liquefied gases under pressure or as vapours of liquefied gases. As an example, nitrous oxide is supplied in a cylinder in liquid form, with an equilibrium vapour pressure of 44.4 bar g at 15° C. Such vapours are not permanent or true gases as they are liquefiable by pressure or temperature around ambient conditions.

A compressed gas cylinder is a pressure vessel designed to contain gases at high pressures, i.e. at pressures significantly greater than atmospheric pressure. Compressed gas cylinders are used in a wide range of markets, from the low cost general industrial market, through the medical market, to higher cost applications, such as electronics manufacture utilising high purity corrosive, toxic or pyrophoric specialty gases. Commonly, pressurised gas containers comprise steel, aluminium or composites and are capable of storing compressed, liquefied or dissolved gases with a maximum filling pressure up to 450 bar g for most gases, and up to 900 bar g for gases such as hydrogen and helium.

In many instances, it is desirable, and sometimes critical, to know the type of gas either inside a cylinder or at a point downstream of a cylinder; for example, in a pipe during a welding process. An example of such a situation would be to know when purging has occurred.

Molecular weights are commonly measured using mass spectrometers. Such arrangements measure the mass to charge ratio of a gas in order to determine the molecular weight directly. A commonly used arrangement is a matrix-assisted laser desorption/ionization source in combination with a time-of-flight mass analyzer (known as MALDI-TOF). However, such arrangements are bulky, expensive and unsuitable for many applications where portability and cost may be of relevance.

An alternative type of meter which may be utilised to measure molecular weights is a vibratory gas density meter such shown and described in "GD series Vibratory Gas Density Meters", Suzuki et al, Yokogawa Technical Report No 29 (2000). Such an arrangement comprises a thin-walled metallic cylinder arranged such that gas is able to flow inside and outside the cylinder. Two pairs of piezoelectric elements are located on the cylinder—a pair of drive elements and a pair of detection elements. The gas density is obtained from a measurement of two different resonant frequencies to compensate for variations due to temperature. The resonant frequencies used are very low and of the order of a few hundred Hz.

The above arrangement is complex, relatively expensive and highly vulnerable to vibration effects. This is because the resonant frequencies used are comparable to the frequencies generated by external vibrations. Additionally, a complicated excitation and detection arrangement is required to compensate for temperature effects.

According to a first aspect of the present invention, there is provided a method of measuring the molecular weight of a gas using a high-frequency planar piezoelectric crystal oscillator in contact with the gas, the method comprising; a) utilising said piezoelectric crystal oscillator to measure the density of the gas by: utilising a drive circuit to drive the piezoelectric oscillator such that the piezoelectric crystal oscillator resonates at a single resonant frequency; and measuring said single resonant frequency of said piezoelectric crystal to determine the density of gas; and b) determining, from the density, determined or pre-determined pressure and determined or pre-determined temperature of the gas, the molecular weight of the gas.

By providing such a method, the molecular weight of a gas (or average molecular weight in the case of a gaseous mixture) can easily be determined using a robust and relatively inexpensive piezoelectric crystal oscillator, for example, a quartz crystal oscillator. Such an oscillator functions both as an excitation source (by oscillating in response to being driven by a drive circuit) and a detector (by having a single resonant frequency which is dependent upon the environment in which the oscillator is located).

A planar crystal oscillator is compact and robust and, as a result, is relatively unaffected by environmental disturbances. Further, because the oscillation frequency of the oscillator is high (of the order of kHz), the oscillator is relatively unaffected by localised vibrations (which tend to have frequencies of the order of Hz). This is in contrast to known molecular weight detection arrangements.

In one embodiment, the method comprises measuring the pressure of the gas.

In one embodiment, the pressure of the gas is measured using an electronic pressure sensor. In one embodiment, the electronic pressure sensor comprises a piezo-resistive diaphragm sensor.

In an embodiment, the pre-determined pressure of the gas is the fixed output pressure of a gas regulator located upstream of said oscillator.

In an embodiment, the pre-determined pressure of the gas is atmospheric pressure.

In an embodiment, the method further comprises measuring the temperature of the gas with a temperature sensor. In one embodiment, the temperature sensor comprises a thermistor or a temperature-dependent resistor.

In an embodiment, the quartz crystal comprises at least one tine. In one arrangement, said piezoelectric crystal oscillator comprises at least two planar tines.

In an embodiment, the quartz crystal is AT cut or SC cut.

In a variation, the surface of the quartz crystal is directly exposed to the gas.

In one embodiment, said piezoelectric crystal oscillator has a resonant frequency of 32 kHz or greater.

In one embodiment, the sensor assembly comprises a power source. In one arrangement, the power source comprises a lithium-ion battery.

In one embodiment, the sensor assembly comprises a processor.

According to a second embodiment of the present invention, there is provided a meter for measuring the molecular weight of a gas, the meter comprising a housing having an inlet and an interior for receiving said gas to be measured, a sensor assembly comprising a high-frequency planar piezoelectric crystal oscillator located within said housing so that, in use, the piezoelectric crystal oscillator is in contact with said gas, said sensor assembly being arranged: to drive the piezoelectric crystal oscillator such that the piezoelectric crystal oscillator resonates at a single resonant frequency; to measure said single resonant frequency of said piezoelectric crystal oscillator to determine the density of gas; and to determine from the density, determined or pre-determined pressure of the gas and determined or pre-determined temperature of the gas, the molecular weight of the gas.

By providing such an arrangement, the molecular weight of a gas (or average molecular weight in the case of a gaseous mixture) can easily be determined using a robust and relatively inexpensive piezoelectric crystal oscillator, for example, a quartz crystal oscillator. Such an oscillator functions both as an excitation source (by oscillating in response to being driven by a drive circuit) and a detector (by having a single resonant frequency which is dependent upon the environment in which the oscillator is located).

A planar crystal oscillator is compact and robust and, as a result, is relatively unaffected by environmental disturbances. Further, because the oscillation frequency of the oscillator is high (of the order of kHz), the oscillator is relatively unaffected by localised vibrations (which tend to have frequencies of the order of Hz). This is in contrast to known molecular weight detection arrangements.

In one embodiment, the meter further comprises one or more of a drive circuit, a processor and a power source.

In one embodiment, the sensor assembly comprises a drive circuit comprising a Darlington pair arranged in a feedback configuration from a common emitter amplifier.

In one embodiment, the meter further comprises a pressure sensor for measuring the pressure of the gas.

In one embodiment, said pressure sensor is an electronic pressure sensor. In one embodiment, the electronic pressure sensor comprises a piezo-resistive diaphragm sensor.

In one embodiment, the meter is located downstream of a fixed pressure regulator, and the pressure of the gas has a predetermined value based on the output of said fixed pressure regulator.

In one embodiment, the meter further comprises a restricted orifice upstream of said inlet and an outlet to atmosphere downstream of said inlet, wherein said predetermined pressure of gas is atmospheric pressure.

In an embodiment, the method further comprises measuring the temperature of the gas with a temperature sensor. In one embodiment, the temperature sensor comprises a thermistor or a temperature-dependent resistor.

In an embodiment, the quartz crystal comprises at least one tine. In a variation, the quartz crystal comprises a pair of planar tines.

In an embodiment, the quartz crystal is AT cut or SC cut.

In a variation, the surface of the quartz crystal is directly exposed to the gas.

In one embodiment, the piezoelectric crystal oscillator has a resonant frequency of 32 kHz or greater.

In one embodiment, the meter comprises a filter located in the inlet. In an embodiment, the filter has a pore size in the range of 5 to 10 µm.

In one embodiment, the meter comprises a heater element located within the housing. In an embodiment, the heater element is located adjacent the piezoelectric crystal oscillator. In a further arrangement, the heater element is located in contact with the piezoelectric crystal oscillator.

In one embodiment, the sensor assembly comprises a power source. In one arrangement, the power source comprises a lithium-ion battery.

In one embodiment, the sensor assembly comprises a processor.

In one embodiment, the meter comprises a display.

In an embodiment, the meter comprises an antenna connected to the sensor assembly and arranged to enable wireless transmission of data from the meter. In an embodiment, the meter is operable to transmit wirelessly data to a remote display unit.

According to a third embodiment of the present invention, there is provided a computer program product executable by a programmable processing apparatus, comprising one or more software portions for performing the steps of the first aspect.

According to a fourth embodiment of the present invention, there is provided a computer usable storage medium having a computer program product according to the fourth aspect stored thereon.

Additionally, there is provided a gas mixer arrangement, the gas mixer arrangement comprising a first gas source for supplying a first gas, a second gas source for supplying a second gas different from said first gas, and a mixer located downstream of the first and second gas sources and arranged, in use, to mix the first and second gases to provide a mixed gas, the gas mixer arrangement further comprising a meter arranged to measure the average molecular weight of the mixed gas and to control the relative proportion of the first and second gases in said mixed gas in response to the measured average molecular weight of said mixed gas.

In one embodiment, the first and second gas sources each comprise a pressure regulation device arranged to control selectively the flow of gas from the respective gas source. In one embodiment, one or each of said pressure regulation devices comprises a pressure regulator or a valve.

In one embodiment, the meter controls at least one of the pressure regulation devices in response to the measured average molecular weight of the mixed gas. In one embodiment, at least one of the pressure regulation devices is an electronic pressure regulation device. In one embodiment, at least one of the pressure regulation devices comprises a solenoid valve.

In one embodiment, the meter comprises a sensor assembly including a piezoelectric crystal oscillator which, in use, is in contact with said mixed gas, said sensor assembly being arranged: to drive the piezoelectric crystal oscillator such that the piezoelectric crystal oscillator resonates at a resonant frequency; to measure the resonant frequency of said piezoelectric crystal oscillator to determine the density of gas; and to determine from the density, determined or pre-determined pressure of the gas and determined or pre-determined temperature of the gas, the molecular weight of the gas.

In an embodiment, the meter comprises the meter of the second aspect.

Embodiments of the present invention will now be described in detail with reference to the accompanying drawings, in which:

FIG. 1 shows a schematic view of a gas cylinder assembly 10 according to an embodiment of the invention.

Figure 1:
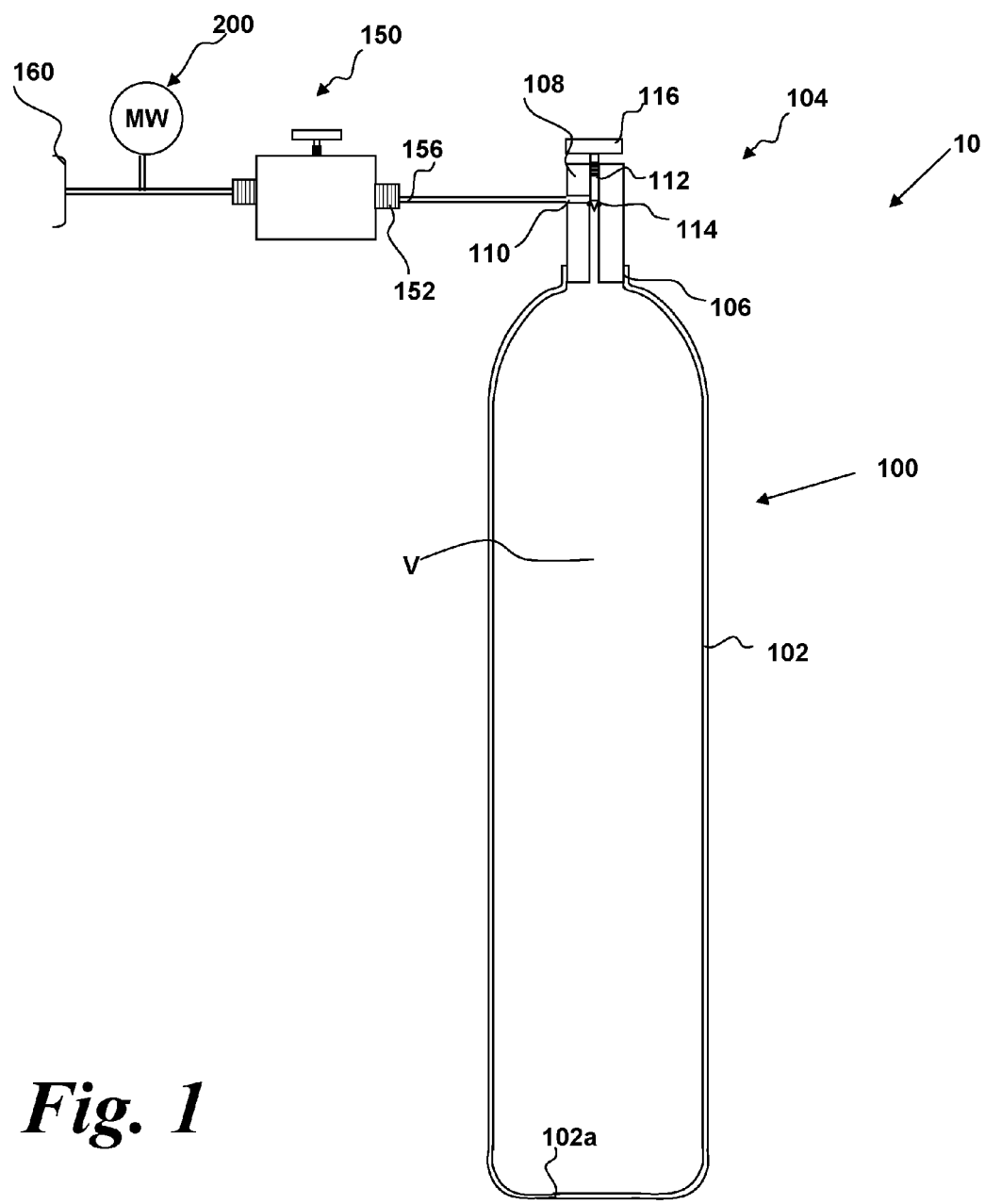
FIG. 1 is a schematic diagram of a gas cylinder and regulator assembly.

FIG. 1 shows a schematic view of a situation in which the present invention may be used. A gas cylinder 100, regulator 150 and molecular weight meter 200 are provided.

The gas cylinder 100 has a gas cylinder body 102 and a valve 104. The gas cylinder body 102 comprises a generally cylindrical pressure vessel having a flat base 102a arranged to enable the gas cylinder assembly 10 to stand unsupported on a flat surface.

The gas cylinder body 102 is formed from steel, aluminium and/or composites material and is adapted and arranged to withstand internal pressures up to approximately 900 bar g. An aperture 106 is located at a proximal end of the gas cylinder body 102 opposite to the base 102a and comprises a screw thread (not shown) adapted to receive the valve 104.

The gas cylinder 100 defines a pressure vessel having an internal volume V. Any suitable fluid may be contained within the gas cylinder 100. However, the present embodiment relates, but is not exclusively limited to, purified permanent gases which are free from impurities such as dust and/or moisture. Non-exhaustive examples of such gases may be: Oxygen, Nitrogen, Argon, Helium, Hydrogen, Methane, Nitrogen Trifluoride, Carbon Monoxide, Krypton or Neon.

The valve 104 comprises a housing 108, an outlet 110, a valve body 112 and a valve seat 114. The housing 108 comprises a complementary screw thread for engagement with the aperture 106 of the gas cylinder body 102. The outlet 110 is adapted and arranged to enable the gas cylinder 100 to be connected to other components in a gas assembly; for example, hoses, pipes, or further pressure valves or regulators. The valve 104 may, optionally, comprise a VIPR (Valve with Integrated Pressure Reduction). In this situation, the regulator 150 may be omitted.

The valve body 112 can be axially adjusted towards or away from the valve seat 114 by means of rotation of a graspable handle 116 selectively to open or to close the outlet 110. In other words, movement of the valve body 112 towards or away from the valve seat 112 selectively controls the area of the communication passageway between the interior of the gas cylinder body 102 and the outlet 110. This, in turn, controls the flow of gas from the interior of the gas cylinder assembly 100 to the external environment.

A regulator 150 is located downstream of the outlet 110. The regulator 150 has an inlet 152 and an outlet 154. The inlet 152 of the regulator 150 is connected to an inlet pipe 156 which provides a communication path between the outlet 110 of the gas cylinder 100 and the regulator 150. The inlet 152 of the regulator 150 is arranged to receive gas at a high pressure from the outlet 110 of the gas cylinder 100. This may be any suitable pressure; however, generally, the pressure of gas exiting the outlet 110 will be in excess of 20 bar and more likely to be in the region of 100-900 bar.

The outlet 154 is connected to an outlet pipe 158. A coupling 160 is located at the distal end of the outlet pipe 158 and is adapted for connection to further pipes or devices (not shown) for which the gas is required.

A molecular weight meter 200 is located in communication with the outlet pipe 158 between the outlet 154 and the coupling 160. The molecular weight meter 200 is located immediately downstream of the regulator 150 and is arranged to determine the molecular weight of the gas (or average molecular weight of a gas mixture) downstream of the regulator 150.

Figure 2:
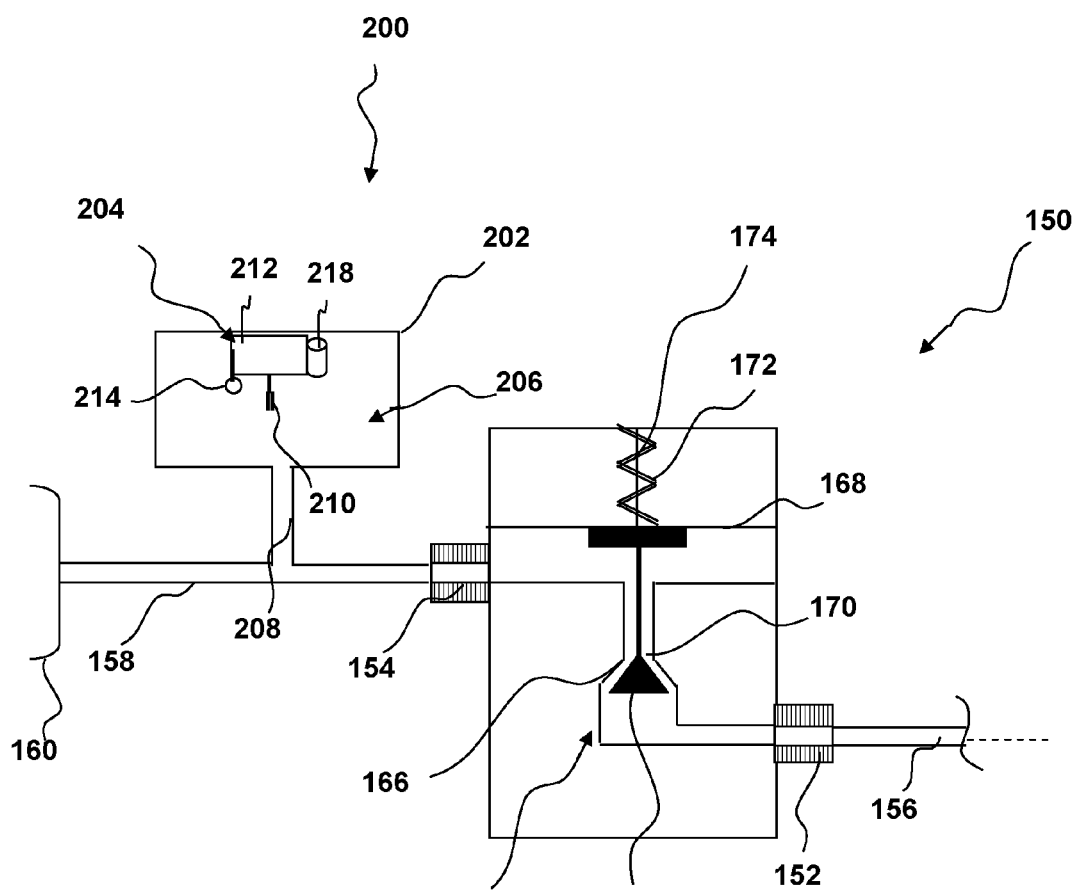
FIG. 2 is a schematic diagram showing a regulator assembly and a molecular weight meter according to a first embodiment of the invention.

The regulator 150 and molecular weight meter 200 according to a first embodiment of the present invention are shown in greater detail in FIG. 2.

In this embodiment, the regulator 150 comprises a single diaphragm regulator. However, the skilled person would be readily aware of variations that could be used with the present invention; for example, a two diaphragm regulator or other arrangement.

The regulator 150 comprises a valve region 162 in communication with the inlet 152 and outlet 154. The valve region 162 comprises a poppet valve 164 located adjacent a valve seat 166. The poppet valve 164 is connected to a diaphragm 168 which is configured to enable translational movement of the poppet valve 164 towards and away from the valve seat 166 to close and open respectively an aperture 170 therebetween.

The diaphragm 168 is resiliently biased by a spring 172 located about a shaft 174.

The regulator 150 is operable to receive gas from the outlet 110 at full cylinder pressure (e.g. 100 bar), but to deliver gas at a substantially constant fixed low pressure (e.g. 5 bar) to the outlet 154. This is achieved by a feedback mechanism whereby the pressure of gas downstream of the aperture 170 is operable to act on the diaphragm 168 in opposition to the biasing force of the spring 172. In the embodiment of FIG. 2, the regulator 150 is a fixed pressure regulator and is arranged to deliver gas from the outlet 154 at a known, fixed pressure. The pressure is determined by the relative biasing force of the spring 172.

Should the pressure of gas in the region adjacent the diaphragm 168 exceed the specified level, the diaphragm 168 is operable to move upwards (relative to FIG. 2). As a result, the poppet valve 164 is moved closer to the valve seat 166, reducing the size of the aperture 170 and, consequently, restricting flow of gas from the inlet 152 to the outlet 154. In general, the competing forces of the resistance of the spring 172 and the pressure of the gas will result in an equilibrium position of the diaphragm and, consequently, delivery of a constant pressure of gas at the outlet 154.

The molecular weight meter 200 comprises a housing 202 and a sensor assembly 204. The housing 202 may comprise any suitable material; for example, steel, aluminium or composites. The housing has an interior 206 which is in communication with the interior of the outlet pipe 158 via a short feed pipe 208. Consequently, the interior 206 of the housing 202 is at the same pressure as the interior of the outlet pipe 158. In use, the housing 202 is generally sealed and isolated from the external atmosphere. The molecular weight meter 200 is arranged to measure the molecular weight of the gas within the housing 202. Alternatively, the molecular weight meter 200 may measure the average molecular weight of a homogeneous mixture of gases within the housing 202.

Alternatively, the housing 202 could be provided as part of the outlet pipe 158. For example, a part of the outlet pipe 158 could be widened to accommodate the sensor assembly 204. Alternatively, only part of the sensor assembly 204 may be located within the pipe 158, with the remainder being located outside or spaced therefrom.

Additionally, the housing 202 may form an integral part of the regulator 150. For example, the sensor assembly 204 may be located entirely within the outlet 154 of the regulator 150. The skilled person would be readily aware of variations and alternatives which fall within the scope of the present invention.

The sensor assembly 204 comprises a quartz crystal oscillator 210 connected to a drive circuit 212, a temperature sensor 214 and a battery 216. These components are located within the housing 202.

The drive circuit 212 and quartz crystal oscillator 210 will be described in detail later with reference to FIGS. 6 and 7. The temperature sensor 214 comprises a thermistor. Any suitable thermistor may be used. High accuracy is not required from the thermistor. For example, an accuracy of 0.5° C. is suitable for this embodiment. Consequently, cheap and small components can be used.

A processor 230 (shown and described later with reference to FIG. 8) may also be provided, either separately or as part of the drive circuit 212.

In this arrangement, the quartz crystal oscillator 210 is constantly under isostatic pressure within the housing 202 of the molecular weight meter 200 and, consequently, do not experience a pressure gradient. In other words, any mechanical stress originating from the pressure difference between external atmosphere and the internal components of the molecular weight meter 200 is expressed across the housing 202.

However, this need not be so. For example, only the quartz crystal oscillator 210 and the temperature sensor 214 may be located within the housing 202, with the remainder of the sensor assembly 204 being located externally thereto.

The inventors have found that only a few components of the sensor assembly 204 are sensitive to high pressure. In particular, larger components such as batteries can be susceptible to high pressures. However, it has been found that lithium ion batteries perform particularly well under the high pressures encountered within the gas cylinder 100. Consequently, the battery 216 comprises lithium ion cells. However, alternative suitable power sources would be readily be contemplated by the skilled person.

The location of the sensor assembly 204 entirely within the housing 202 provides additional flexibility when configuring regulators 150. In particular, location of relatively fragile electronic components entirely within the strong metal or composite walls of the housing 202 provides considerable protection from environmental or accidental damage. This is particularly important, for example, in storage areas or depots, where gas cylinders 100 comprising regulators 150 are located adjacent gas cylinders, heavy machinery or rough surfaces.

Additionally, the internal location of the sensor assembly 204 protects these components from environmental conditions such as salt, water and other contaminants. This would allow, for example, a high impedance circuit which is highly sensitive to salt and water damage to be used as part of the sensor assembly 204.

The benefits of internal location of the sensor assembly 204 are unique to solid state sensor devices such as the quartz crystal oscillator 210. For example, a conventional pressure sensor such as a Bourdon gauge cannot be located in this manner. Whilst a crystal-based sensor can operate totally immersed in gas at constant pressure, a conventional pressure sensor is unable to measure isostatic pressure and requires a pressure gradient in order to function. Consequently, a conventional pressure gauge must be located between the high pressure to be measured and the atmosphere. This increases the risk of damage to external components of the molecular weight meter 200.

Figure 3:
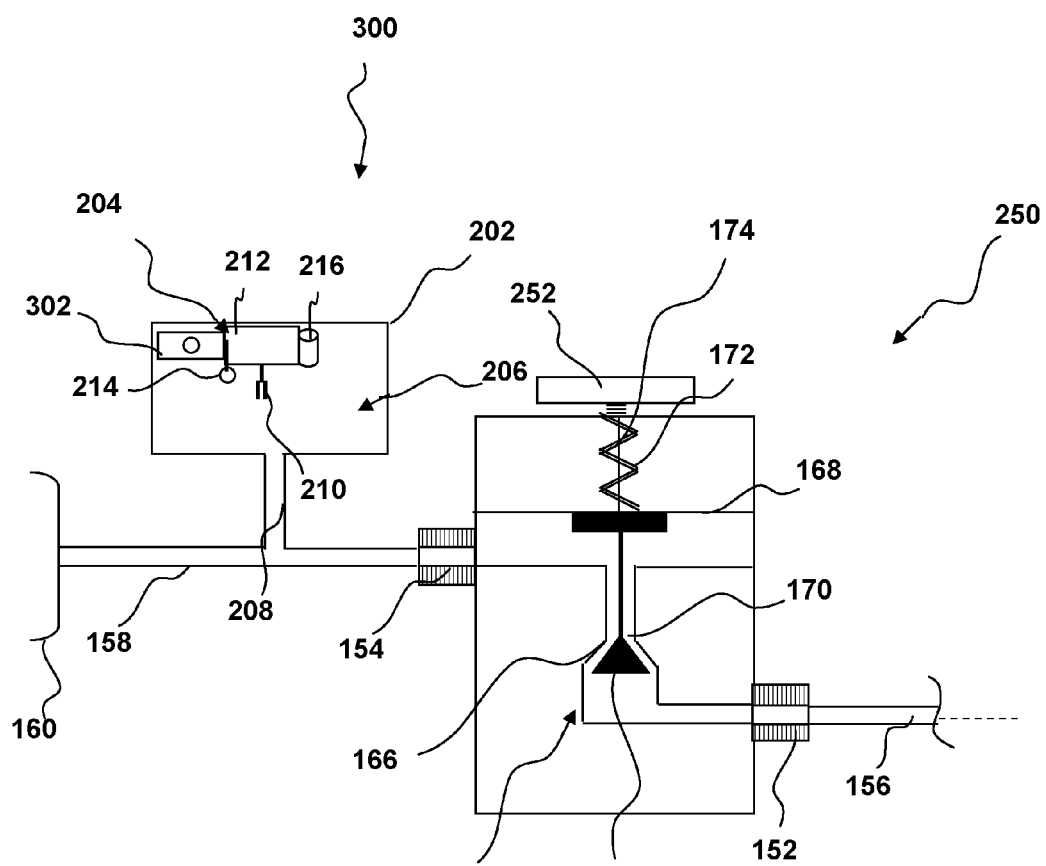
FIG. 3 is a schematic diagram showing a regulator assembly and a molecular weight meter according to a second embodiment of the invention.

A second embodiment of the invention is shown in FIG. 3. The features of the second embodiment shown in FIG. 3 which are in common with the first embodiment of FIG. 2 are allocated the same reference numerals and will not be described again here.

In the embodiment of FIG. 3, the regulator 250 differs from the regulator 150 of the FIG. 2 embodiment in that the regulator 250 is arranged to provide a variable outlet pressure of gas from the outlet 154.

In this regard, a graspable handle 252 is provided to enable a user to adjust the biasing force of the spring 172. This moves the equilibrium position of the diaphragm 168 and, as a result, adjusts the equilibrium spacing between the poppet valve 164 and the valve seat 166. This enables adjustment of the dimensions of the aperture 170 through which the high pressure gas flow from the outlet 110 can pass.

The pressure may, typically, be varied up to about 20 bar g. However, the skilled person would be readily aware of alternative arrangements and pressures which could be supplied by the regulator 250. Further, the regulator may comprise secondary stages for use in situations such as oxy-acetylene welding where precise regulation of pressure is required.

The second embodiment comprises a molecular weight meter 300. Components of the molecular weight meter 300 in common with the molecular weight meter 200 are allocated the same reference numerals for clarity.

The molecular weight meter 300 is substantially similar to the molecular weight meter 200 of the first embodiment. However, the molecular weight meter 300 further comprises a pressure sensor 302 located within the housing 202. Any suitable pressure sensor may be used.

For example, the pressure sensor 302 may comprise a piezo-resistive diaphragm sensor. Such a pressure sensor typically comprises a machined silicon diaphragm having piezo-resistive strain gauges formed therein. The diaphragm is fused to a silicon or glass backplate. The strain gauges are commonly connected to form a Wheatstone bridge, the output of which is directly proportional to the measured pressure. The output from the pressure sensor 302 can then be inputted to the processor 230.

The skilled person would be readily aware of alternative electronic pressure sensors which could be used with the present invention. In other words, the pressure sensor 302 may comprise any sensor capable of measuring the pressure of a gas and providing an electronic output of that measurement.

In this arrangement, the quartz crystal oscillator 210 and pressure sensor 302 are constantly under isostatic pressure within the housing 202 of the molecular weight meter 200 and, consequently, do not experience a pressure gradient. In other words, any mechanical stress originating from the pressure difference between external atmosphere and the internal components of the molecular weight meter 300 is expressed across the housing 202.

Figure 4:
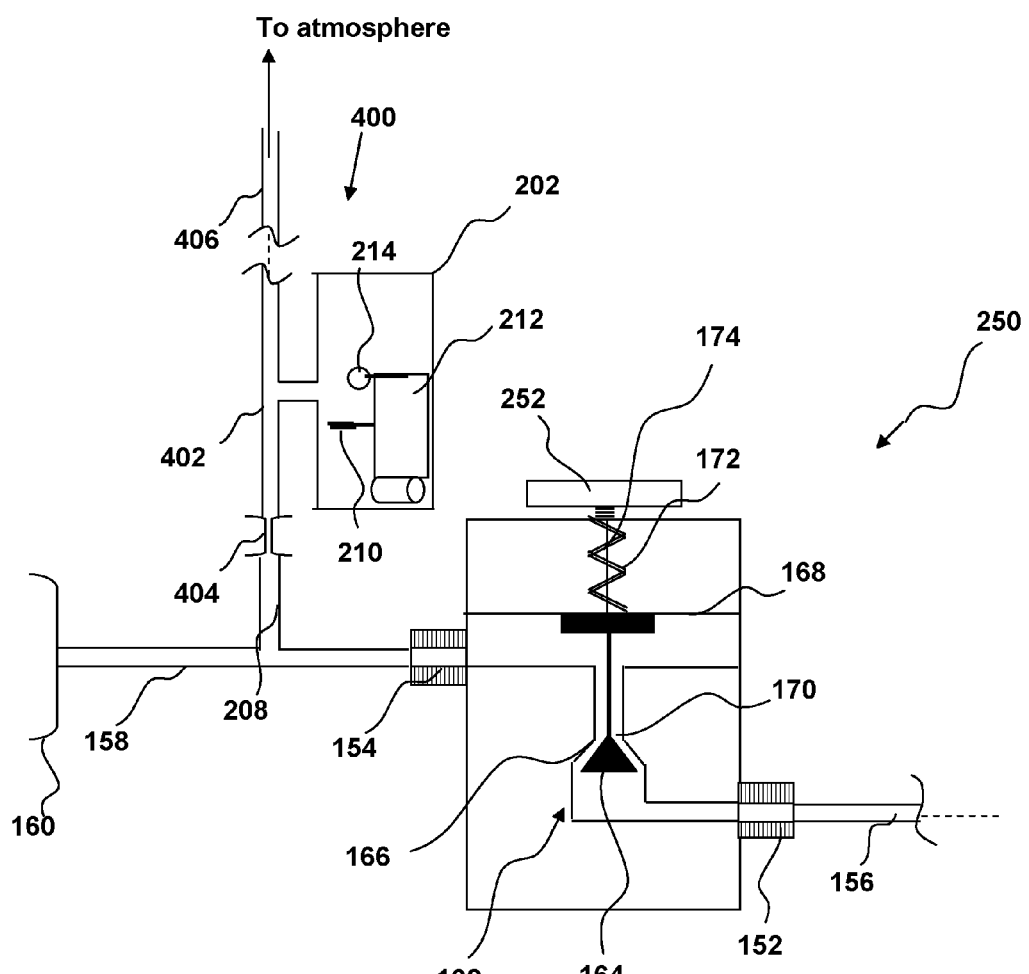
FIG. 4 is a schematic diagram showing a regulator assembly and a molecular weight meter according to a third embodiment of the invention.

A third embodiment of the invention is shown in FIG. 4. The features of the third embodiment shown in FIG. 4 which are in common with the second embodiment of FIG. 3 are allocated the same reference numerals and will not be described again here.

In the embodiment of FIG. 4, the regulator 250 corresponds to the regulator 250 of the second embodiment and is arranged to provide a variable outlet pressure of gas from the outlet 154. The components of the regulator 250 have already been described and will not be described further here.

The third embodiment comprises a molecular weight meter 400. Components of the molecular weight meter 400 in common with the molecular weight meters 200, 300 are allocated the same reference numerals for clarity.

The molecular weight meter 400 is substantially similar to the molecular weight meters 200, 300 of the first and second embodiments. However, the molecular weight meter 400 is operable with a variable pressure regulator 250 without requiring the pressure sensor 302 of the second embodiment.

The molecular weight meter 400 comprises a conduit 402. The interior of the conduit 402 is in communication with the interior 206 of the housing 202. A proximal end of the conduit 402 comprises a restricting orifice 404 located immediately downstream of the short pipe 208 and in communication with the outlet 154. The restricting orifice 404 is arranged to provide a physical restriction to limit the pressure of gas entering the conduit 402 from the outlet 154. Therefore, the pressure of gas within the conduit 402 downstream of the restricting orifice 404 is considerably lower than that in the outlet 154.

A distal end 406 of the conduit 402 is open to atmosphere. The distal end 406 is located at the end of a section of the conduit 402 downstream of the housing 202. For typical applications, a suitable conduit 402 would have a bore in the region of 2 mm and a length of around 100 mm. This is to ensure that there is no back-diffusion of atmospheric gases into the interior 206 of the housing 202 to avoid potential errors in measurement.

Whilst the conduit 402 is shown as essentially linear in FIG. 4, the conduit 402 could be any suitable shape. For example, a more compact arrangement would be to arrange the conduit 402 into a labyrinthine or coil shape in order to fit the conduit into a smaller space.

Consequently, the combined effect of the restricting orifice 404 and remote distal end 406 of the conduit 402 (which is at atmospheric pressure) is that the interior 206 of the housing 202 is always at, or close to, atmospheric pressure. This is irrespective of the pressure of gas downstream of the outlet 154 and upstream of the restricting orifice 404.

As a result, no pressure gauge is required since the pressure can always be assumed to be at atmospheric pressure. Should a correction be required (for example, when operating at high altitudes where atmospheric pressure is lower), this may be manually inputted to the processor 230.

Therefore, under particular conditions, no pressure sensor is needed since the pressure value may be set automatically or manually inputted by a user, and the resulting pressure value used by the processor 230 to determine the molecular weight of the gas or gases being sensed.

Figure 5:
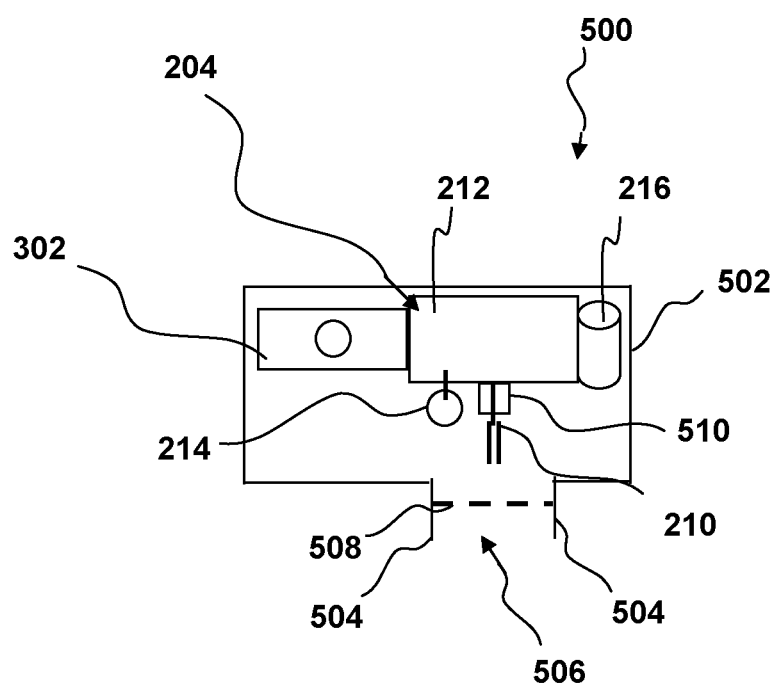
FIG. 5 is a schematic diagram showing a molecular weight meter according to a fourth embodiment of the invention.

A fourth embodiment of the present invention is shown in FIG. 5. The fourth embodiment relates to a molecular weight meter 500. The molecular weight meter 500 may be portable and may be placed in locations where it is desired to determine quickly and easily the type of gas within a specific location; for example, within a pipe during an orbital welding process. Alternatively, the molecular weight meter 500 may be placed at the outlet of a pipe to detect, for example, the purging of one type of gas with another type of gas.

The molecular weight meter 500 comprises a housing 502. The housing 502 has walls 504 which delimit an aperture 506. The aperture 506 provides a communication path between the interior and exterior of the housing 504. The remaining components of the molecular weight meter 500 are similar to those of the molecular weight meters 200, 300, 400 of the first to third embodiments and will not be described any further here.

In order for the quartz crystal oscillator 210 to provide an accurate measurement, the quartz crystal oscillator 210 must be kept free of dirt, moisture and other contamination. Whilst this is not an issue for commercially-supplied packaged gases (which are extremely clean), the molecular weight meter 500 may be used in situations where environmental contamination may be a significant issue.

Consequently, the molecular weight meter 500 is provided with a filter 508 located in the aperture 506. The filter 508 may be of any suitable pore size. Pore sizes are in the 5-10 µm range are particularly suitable for this application. The filter 508 (or a similar filter) may be applied to any of the first to third embodiments described previously.

Alternatively, the filter 508 may be omitted if the aperture 506 is sufficiently small to prevent the ingress of dirt or other contaminants. For example, an aperture size of 0.25 mm would be suitable for use without a filter.

Additionally, the molecular weight meter 500 may be subject to environments where moisture is present. An incorrect measurement may result if any moisture condense on the quartz crystal oscillator 210. Therefore, in order to mitigate these effects, a heater 510 adjacent the quartz crystal oscillator 210 may be provided in order to ensure that moisture does not condense on the oscillator 210. The heater 510 may comprise a single heated wire or may comprise a solid resistive element to convert electrical energy to thermal energy. The heater 510 may be located in contact with the quartz crystal oscillator 210.

If a heater is used, it is desirable that the temperature sensor 214 is located as close as practicable to the quartz crystal oscillator 210 so that an accurate measurement of the temperature of the gas surrounding the quartz crystal oscillator 210 can be made. The heater 510, or any other suitable heater, may also be used with any of the first to third embodiments.

The molecular weight meter 500 is shown in FIG. 5 comprising a pressure sensor 302, in common with the molecular weight meter 300 of the second embodiment. Such an arrangement may be beneficial when used within pressurised apparatus such as high-pressure pipes or within pressure vessels.

However, in situations where the pressure is known to a general degree of accuracy, the pressure sensor 302 may be omitted in the manner of the first and third embodiments. Such a situation may arise when the molecular weight meter 500 is used at ambient atmospheric pressure; for example, when measuring the molecular weight (or average molecular weight) of gas exiting a pipe to atmosphere, or within pipes at atmospheric pressure. In this situation, no pressure sensor is needed since the pressure value may be set automatically or manually inputted by a user, and the resulting pressure value used by the processor 230 to determine the molecular weight of the gas or gases being sensed.

Any of the first to fourth embodiments may additionally comprise a display (not shown) to show a user the results of measurements made on the detected gas. Alternatively, the display may be located remote from the molecular weight meters 200, 300, 400, 500 and the relevant data may be communicated remotely.

For example, any one of the first to fourth embodiments may further comprise an antenna (not shown) for remote communication with, for example, a base station. This will be discussed later. In this case, the antenna may be located outside the housing 202 and connected to the sensor assembly 204 by means of a wire or equivalent connector.

The antenna itself may be adapted and arranged to use any suitable communication protocol; for example, a non-exhaustive list may be RFID, Bluetooth, Infra red (IR), 802.11 wireless, frequency modulation (FM) transmission or a cell network.

Alternatively, one-wire communication may be implemented. One-wire communication needs only a single metallic conductor to communicate: the 'return' path of the circuit is provided by capacitive coupling through the air between the communicating devices. The skilled person would be readily aware of alternatives of the antenna (and associated transmission hardware) which could be used with the embodiments discussed herein.

For example, communication may be effected by means of acoustic transmission from within the cylinder 100. A transmitter located within the housing 202 may effect acoustic transmission. The transmitter may comprise, for example, a simple fixed-frequency piezoelectric resonator.

A complementary receiver is also required and this component may be located remote from the molecular weight meter 200, 300, 400, 500 and may comprise hardware such as, for example, a phase-locked loop tone detector integrated with a microphone.

The sensor assembly 204 will now be described in more detail with reference to FIGS. 6 and 7. The quartz crystal oscillator 210 comprises a planar section of cut quartz. Quartz demonstrates piezoelectric behaviour, i.e. the application of a voltage across the crystal causes the crystal to change shape, generating a mechanical force. Conversely, a mechanical force applied to the crystal produces an electrical charge.

Two parallel surfaces of the quartz crystal oscillator 210 are metallised in order to provide electrical connections across the bulk crystal. When a voltage is applied across the crystal by means of the metal contacts, the crystal changes shape. By application of an alternating voltage to the crystal, the crystal can be caused to oscillate.

The physical size and thickness of the quartz crystal determines the characteristic or resonant frequency of the quartz crystal. Indeed, the characteristic or resonant frequency of the crystal 210 is inversely proportional to the physical thickness between the two metallised surfaces. Quartz crystal oscillators are well known in the art and so the structure of the quartz crystal oscillator 210 will not be described further here.

Additionally, the resonant vibration frequency of a quartz crystal will vary depending upon the environment in which the crystal is located. In a vacuum, the crystal will have a particular frequency. However, this frequency will change in different environments. For example, in a fluid, the vibration of the crystal will be damped by the surrounding molecules and this will affect the resonant frequency and the energy required to oscillate the crystal at a given amplitude.

Further, deposition of surrounding materials onto the crystal will affect the mass of the vibrating crystal, altering the resonant frequency. Such adsorption or deposition of material forms the basis for commonly used selective gas analysers in which an absorbing layer is formed on the crystal and increases in mass as gas is absorbed.

However, in the present case, no coating is applied to the quartz crystal oscillator 210. Indeed, adsorption or deposition of material onto the quartz crystal oscillator 210 is undesirable in the present case since the accuracy of the measurement may be affected.

Figure 6:
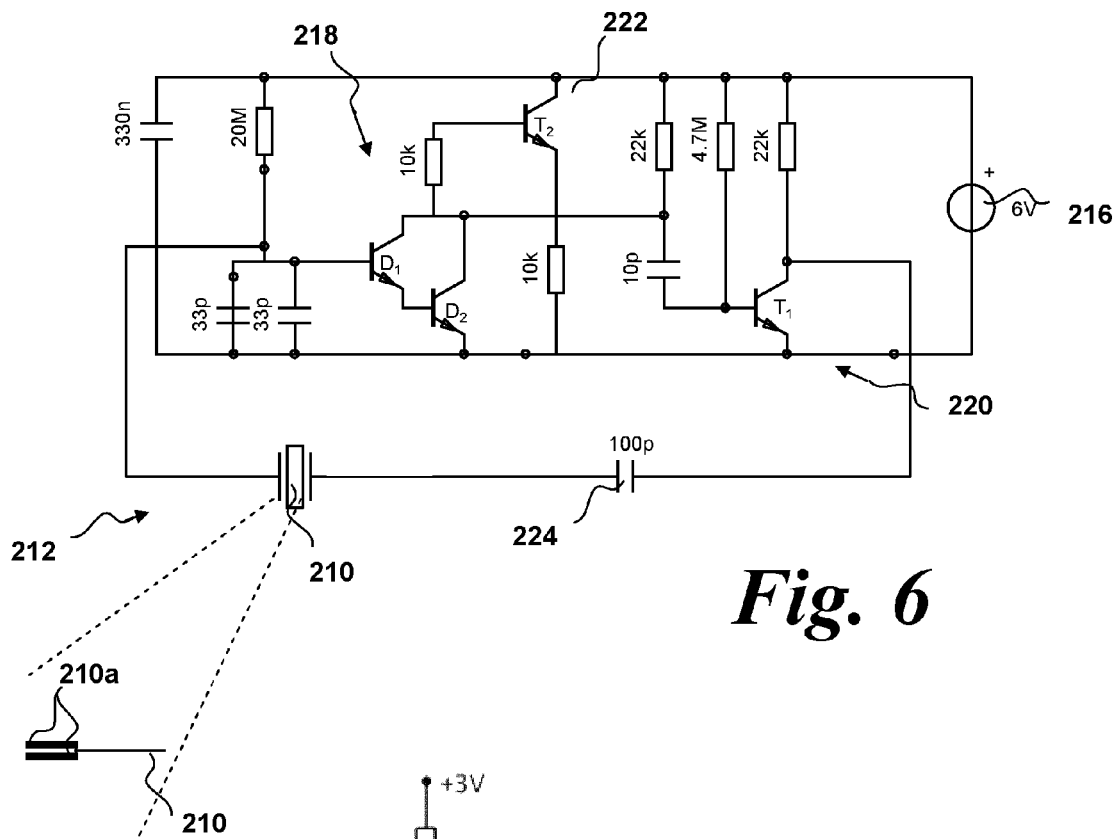
FIG. 6 is a schematic diagram of a drive circuit for use with the any of the first to fourth embodiments.
Figure 7:
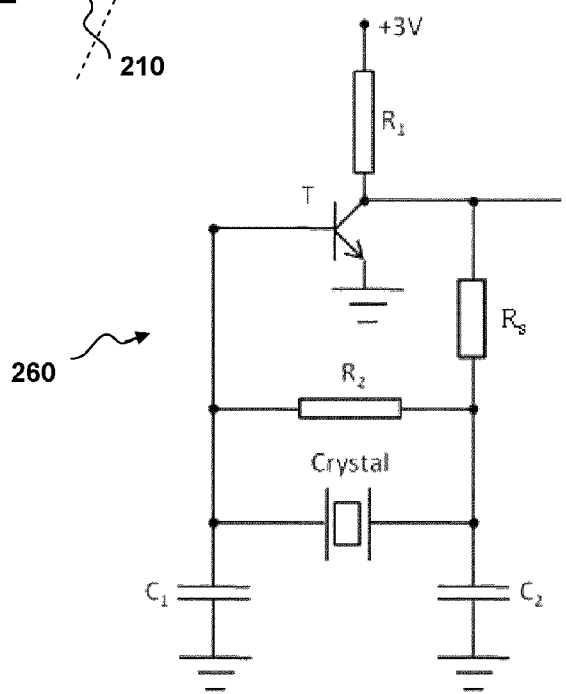
FIG. 7 is a schematic diagram showing an alternative the drive circuit for use with any of the first to fourth embodiments.

As shown in FIG. 6, the quartz crystal oscillator 210 of the present embodiment is tuning fork-shaped and comprises a pair of tines 210a approximately 5 mm long arranged to oscillate at a resonant frequency of 32.768 kHz. The tines 210a are formed in the planar section of quartz. The tines 210a of the fork oscillate normally in their fundamental mode, in which they move synchronously towards and away from each other at the resonant frequency.

Fused (or non-crystalline) quartz has a very low temperature-dependent coefficient of expansion and a low coefficient of elasticity. This reduces the dependence of the fundamental frequency on temperature and, as will be shown, temperature effects are minimal.

Additionally, it is desirable to use quartz which is AT cut or SC cut. In other words, the planar section of quartz is cut at particular angles, so that the temperature coefficient of the oscillation frequency can be arranged to be parabolic with a wide peak around room temperature. Therefore, the crystal oscillator can be arranged such that the slope at top of the peak is precisely zero.

Such quartz crystals are commonly available at relative low cost. In contrast to the majority of quartz crystal oscillators which are used in vacuo, in the present embodiment the quartz crystal oscillator 210 is exposed to the gas under pressure in the housing 202.

The drive circuit 212 for driving the quartz crystal oscillator 210 is shown in FIG. 6. The drive circuit 212 must meet a number of specific criteria. Firstly, the quartz crystal oscillator 210 of the present invention may be exposed to a range of gas pressures; potentially, the pressures may vary from atmospheric pressure (when the gas cylinder 100 is empty) to around 900 bar g if the gas cylinder contains a pressurised gas such as hydrogen. Thus, the quartz crystal oscillator 210 is required to operate (and restart after a period of non-use) under a wide range of pressures.

Consequently, the quality (Q) factor of the quartz crystal oscillator 210 will vary considerably during use. The Q factor is a dimensionless parameter relating to the rate of damping of an oscillator or resonator. Equivalently, it may characterise the bandwidth of a resonator relative to its centre frequency.

In general, the higher the Q factor of an oscillator, the lower the rate of energy loss relative to the stored energy of the oscillator. In other words, the oscillations of a high Q factor oscillator reduce in amplitude more slowly in the absence of an external force. Sinusoidally driven resonators having higher Q factors resonate with greater amplitudes at the resonant frequency but have a smaller bandwidth of frequencies around that frequency for which they resonate.

The drive circuit 212 must be able to drive the quartz crystal oscillator 210 despite the changing Q factor. As the pressure in the gas cylinder 100 increases, the oscillation of the quartz crystal oscillator 210 will become increasingly damped, and the Q factor will fall. The falling Q factor requires a higher gain to be provided by an amplifier in the drive circuit 212. However, if too high an amplification is provided, the drive circuit 212, the response from the quartz crystal oscillator 210 may become difficult to distinguish. In this case, the drive circuit 212 may simply oscillate at an unrelated frequency, or at the frequency of a non-fundamental mode of the quartz crystal oscillator 210.

As a further limitation, the drive circuit 212 must be low power in order to run on small low power batteries for a long time with or without supplementary power such as photovoltaic cells.

The drive circuit 212 will now be described with reference to FIG. 6. In order to drive the quartz crystal oscillator 210, the drive circuit 212 essentially takes a voltage signal from the quartz crystal oscillator 210, amplifies it, and feeds that signal it back to the quartz crystal oscillator 210. The fundamental resonant frequency of the quartz crystal oscillator 210 is, in essence, a function of the rate of expansion and contraction of the quartz. This is determined in general by the cut and size of the crystal.

However, external factors also affect the resonant frequency. When the energy of the generated output frequencies matches the losses in the circuit, an oscillation can be sustained. The drive circuit 212 is arranged to detect and maintain this oscillation frequency. The frequency can then be measured by the processor 230, used to calculate the appropriate property of the gas required by the user and, if required, output to a suitable display means (as will be described later).

The drive circuit 212 is powered by a 6 V battery 216. The battery 216, in this embodiment, comprises a lithium ion battery. However, alternative power sources will be readily apparent to the person skilled in the art; for example, other battery types both rechargeable and non-rechargeable and a solar cell arrangement.

The drive circuit 212 further comprises a Darlington pair Common Emitter amplifier 218. A Darlington pair comprises a compound structure consisting of two bipolar NPN transistors configured such that the current amplified by a first of the transistor is amplified further by the second one. This configuration enables a higher current gain to be obtained when compared to each transistor being taken separately. Alternative, PNP bipolar transistors may be used.

The Darlington pair 218 is arranged in a feedback configuration from a single transistor ($T_1$) Common Emitter amplifier 220. A NPN bipolar junction transistor is shown in FIG. 4. However, the skilled person would be aware of alternative transistor arrangements which may be used; for example, a bipolar junction PNP transistor or Metal Oxide Semiconductor Field Effect Transistors (MOSFETs).

As a variation, automatic gain control (not shown) could be implemented in the feedback loop between the Darlington pair 218 and the Common Emitter amplifier 220. This may take the form of a potentiometer, variable resistor or other suitable component located in place of, for example, the rightmost 22 k resistor shown in FIG. 6.

Automatic gain control enables compensation for changes in Q-factor with pressure and changes in supply voltage (for example, under low battery conditions). Automatic gain control may be particularly applicable for low pressure applications.

The drive circuit 212 comprises a further NPN emitter follower transistor $T_2$ which acts as a buffer amplifier 222. The buffer amplifier 222 is arranged to function as a buffer between the circuit and the external environment. However, this feature is optional and may not required; for example, a FET could be directly connected to drive the circuit 212.

A capacitor 224 is located in series with the quartz crystal oscillator 210. The capacitor 224, in this example, has a value of 100 pF and enables the drive circuit 212 to drive the quartz crystal oscillator 210 in situations where the crystal has become contaminated, for example by salts or other deposited materials.

An alternative drive circuit 260 will now be described with reference to FIG. 7. The drive circuit shown in FIG. 7 is configured similarly to a Pierce oscillator. Piece oscillators are known from digital IC clock oscillators. In essence, the drive circuit 260 comprises a single digital inverter (in the form of a transistor) T, three resistors $R_1$, $R_2$ and $R_S$, two capacitors $C_1$, $C_2$, and the quartz crystal oscillator 210.

In this arrangement, the quartz crystal oscillator 210 functions as a highly selective filter element. Resistor $R_1$ acts as a load resistor for the transistor T. Resistor $R_2$ acts as a feedback resistor, biasing the inverter T in its linear region of operation. This effectively enables the inverter T to operate as a high gain inverting amplifier. Another resistor $R_S$ is used between the output of the inverter T and the quartz crystal oscillator 210 to limit the gain and to dampen undesired oscillations in the circuit.

The quartz crystal oscillator 210, in combination with $C_1$ and $C_2$ forms a Pi network band-pass filter. This enables a 180 degree phase shift and a voltage gain from the output to input at approximately the resonant frequency of the quartz crystal oscillator. The above described drive circuit 260 is reliable and cheap to manufacture since it comprises relatively few components.

As discussed above, the sensor assembly 204 may include a processor 230 which receives inputs from the quartz crystal oscillator 210 and drive circuit 212. The processor 230 may comprise and suitable arrangement, such as an ASIC or FPGA.

Figure 8:
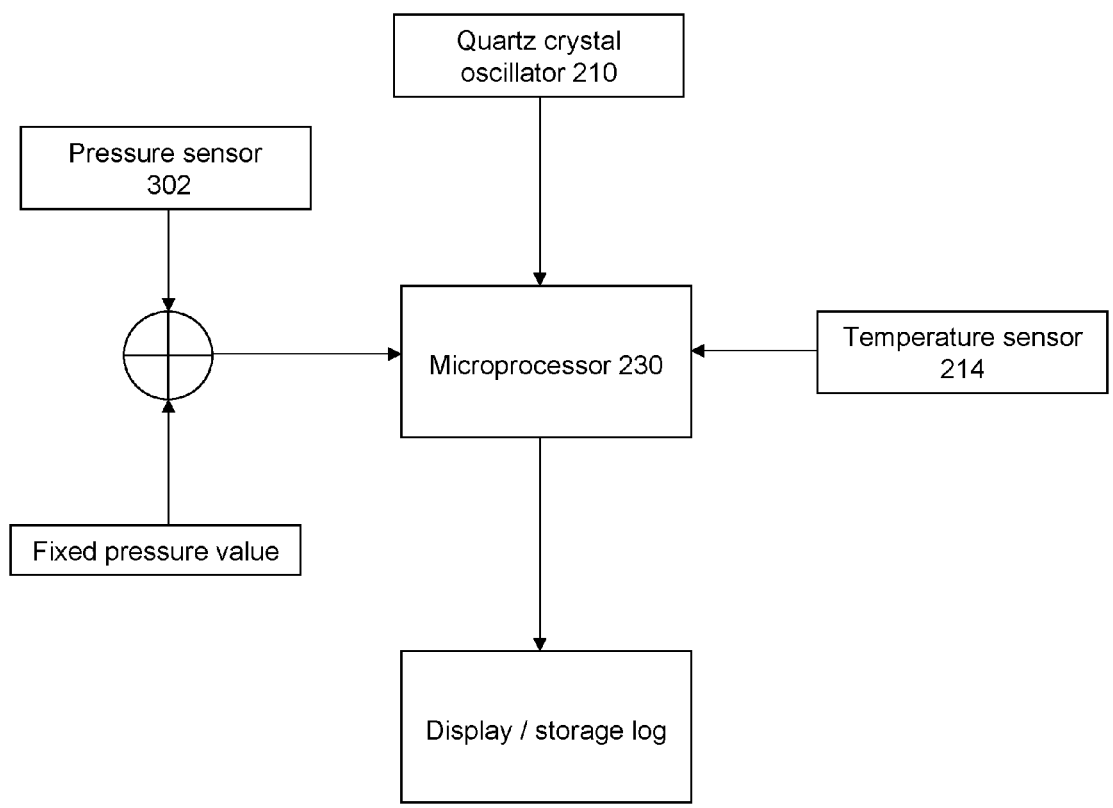
FIG. 8 is a schematic diagram showing the inputted and outputted parameters of a processor for use with any of the first to fourth embodiments.

The processor 230 is programmed to calculate and, if required, display and communicate a determination of the molecular weight of the gas (or average molecular weight of a homogenous mixture of gases). A schematic of the main inputs and outputs of the processor 230 are shown in FIG. 8.

When used with the quartz crystal oscillator 210, the processor 230 may be configured to measure the frequency f or period of the signal from the drive circuit 212. This may be achieved by, for example, counting oscillations over a fixed time, and convert that frequency into a density value using an algorithm or look-up table. This value is passed to the processor 230.

The processor 230 also receives the measured temperature T from the temperature sensor 214. Further, the processor 230 receives a pressure value from either a pressure sensor 302 (if present) or from a fixed pressure value. This value may be set automatically; for example, in situations where the molecular weight meter 400, 500 is to be used only at atmospheric pressure or is to be used on the outlet of a fixed pressure regulator as is the case for the molecular weight meter 200. In this situation, the fixed pressure value is inputted to the processor 230. Alternatively, the fixed pressure value may be inputted manually by a user.

The processor 230 is arranged to perform, based on the supplied inputs, a calculation to determine the molecular weight of the gas in which the quartz crystal oscillator 210 is immersed.

Once the molecular weight has been determined, this data may be stored in a local memory, may be displayed on a display screen or may be transmitted to a remote station.

The processor 230 may, optionally, be designed for mass production to be identical in all molecular weight meter 200, with different features in the software and hardware enabled for different gases.

Additionally, the processor 230 may also be configured to minimise power consumption through implementation of standby or "sleep" modes which may cover the processor 230 and additional components such as the drive circuit 212 and quartz crystal oscillator 210.

Various schemes may be implemented; for example, the processor 230 may be on standby for 10 seconds out of every 11 seconds. Further, the processor 230 may control the quartz crystal oscillator 210 and drive circuit 212 such that these components are put on standby for the majority of time, only being switching the more power-hungry components on for ½ second every 30 seconds.

The theory and operation of the sensor assembly 204 will now be described with reference to FIGS. 9 to 13.

The quartz crystal oscillator 210 has a resonant frequency which is dependent upon the density of the fluid in which it is located. Exposing an oscillating tuning fork-type planar crystal oscillator to a gas leads to a shift and damping of the resonant frequency of the crystal (when compared to the resonant frequency of the crystal in a vacuum). There are a number of reasons for this. Whilst there is a damping effect of the gas on the oscillations of the crystal, the gas adjacent the vibrating tines 210a of the tuning fork crystal oscillator 210 increases the effective mass of the oscillator. This leads to a reduction in the resonant frequency of the quartz crystal oscillator according to the motion of a one-sided, fixed elastic beam:

$$\frac{\Delta \omega}{\omega_0} = \frac{\rho t}{2 \rho_q w}\left(c_1 + c_2 \frac{\partial}{t}\right) \quad 1)$$

Where $$\frac{\Delta \omega}{\omega_0}$$

is the relative change in resonant angular frequency, $\rho$ is the gas density, t is the thickness of the quartz oscillator, $\rho_q$ is the density of the quartz oscillator and w is the width of the fork. $c_1$ and $c_2$ are geometrically dependent constants and $\partial$ is the thickness of the surface layer of gas as defined by:

$$\partial = \sqrt{\frac{2\eta}{\rho \omega_0}} \quad 2)$$

Where $\eta$ is the temperature dependent viscosity of the gas.

The two parts of equation 1) relate to a) the additive mass of the gas on the tines of the quartz crystal oscillator 210 and to b) the shear forces arising on the outermost surface layer of the tines during oscillation.

The equation can thus be rewritten in terms of frequency and simplified to:

$$\Delta f = A\rho + B\sqrt{\rho} + C \quad 3)$$

Where $$A = \frac{c_1 t}{2\rho_q w} f_0, \quad B = \frac{c_2}{2\rho_q w}\sqrt{\frac{\eta}{\pi}}\sqrt{f_0},$$

C is an offset constant and $f_0$ is the natural resonant frequency of the crystal in a vacuum.

It has been found by the inventors that a suitably good approximation can be obtained by approximating:

$$\Delta f \approx A\rho \quad 4)$$

Figure 9:
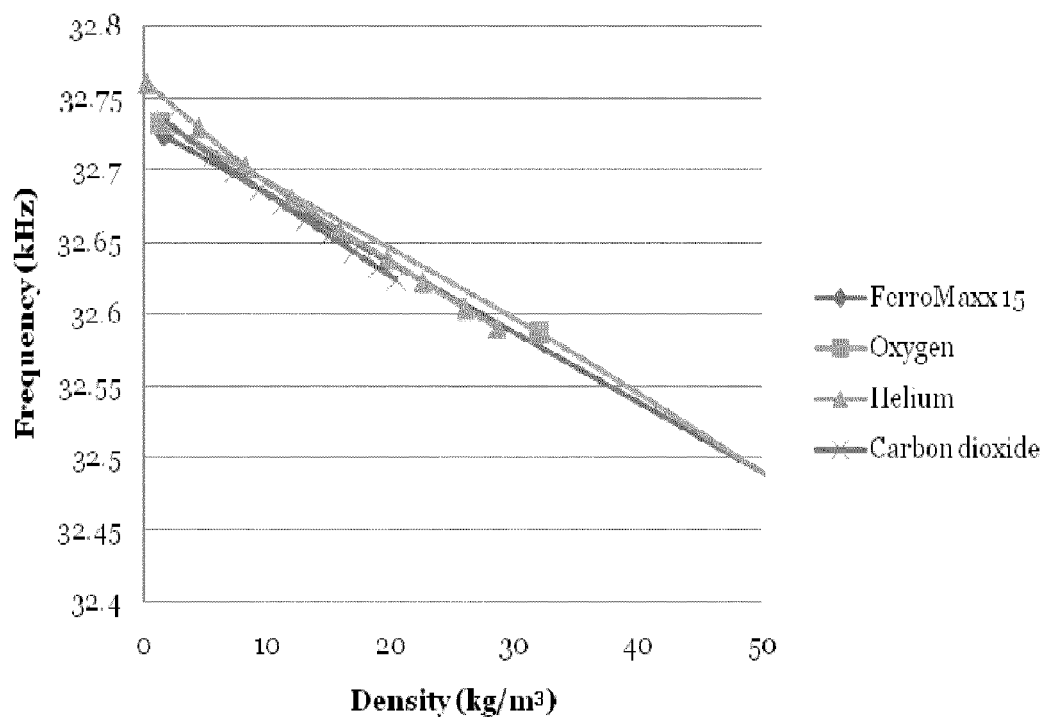
FIG. 9 shows a graph of quartz crystal frequency (kHz) on the Y-axis as a function of density (kg/m$^3$) for a number of different gases.

Consequently, to a good approximation, the change in frequency is proportional to the change in density of the gas to which the quartz crystal oscillator is exposed. FIG. 9 shows, for a number of different gases/gas mixtures, that the resonant frequency of the quartz crystal oscillator 210 varies linearly as a function of density.

In general, the sensitivity of the quartz crystal oscillator 210 is that a 5% change in frequency is seen with, for example, Oxygen gas (having Atomic mass number 32) at 250 bar when compared to atmospheric pressure. Such pressures and gas densities is typical of the storage cylinders used for permanent gases, which are normally between 137 and 450 bar g for most gases, and up to 700 or 900 bar g for helium and hydrogen.

The quartz crystal oscillator 210 is particularly suitable for use as a density sensor forming part of a molecular weight meter for commercially-supplied gases. In order to sense correctly the density of a gas, it is necessary for the gas to be free from dust and droplets of liquids, which is guaranteed with commercially supplied gases, but not with air or in the generality of pressure monitoring situations.

Once the density value is obtained from the quartz crystal oscillator 210, the molecular weight of the gas can be determined from:

$$PV = nRT \quad 5)$$

where P is the pressure of gas, V is the volume of gas, n is the number of moles of gas, R is the gas constant and T is the temperature. Following on to eliminate V:

$$\rho = \frac{M}{V} \quad 6)$$

And $$MW = \frac{M}{n} \quad 7)$$

where MW is the molecular weight of gas and M is the mass of gas. Therefore, substituting for V in equation 5) leads to:

$$MW = \alpha \frac{\rho}{P} \quad 8)$$

where α is a constant equal to RT, where R is the gas constant and T is the absolute temperature in Kelvin. Consequently, for a known pressure, density and temperature of a gas, the molecular weight of the gas (or average molecular weight in the case of a mixture of gases) can be determined. The above derivations assume that the gas is close to an Ideal Gas.

Based on equation 8) above, if the pressure is known (e.g. where the pressure is at atmospheric or the output of a fixed pressure regulator), then only the temperature and density of the gas is needed to provide an accurate determination of molecular weight. Concomitantly, if the pressure and temperature are known to a reasonable degree, the molecular weight of the gas is effectively proportional to the density or, in other words, the resonant frequency of the quartz crystal oscillator multiplied by a predetermined factor.

Consequently, the molecular weight of the gas (or average of a mixture) can be determined from the gradient of pressure as a function of density, where, rearranging equation 8 provides:

$$\rho = \frac{MW}{\alpha} P \quad 9)$$

Figure 10:
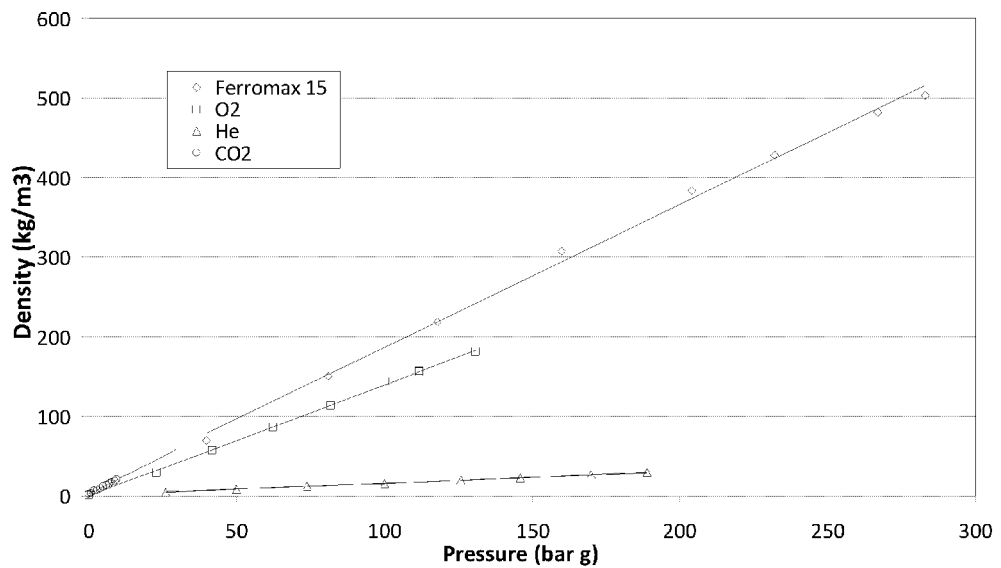
FIG. 10 shows a graph of gas density (in kg/m$^3$) on the Y-axis as a function of pressure (bar g) on the X-axis for Argon, Oxygen and an Argon:Carbon Dioxide:Oxygen mixture at pressures up to 300 bar g.
Figure 11:
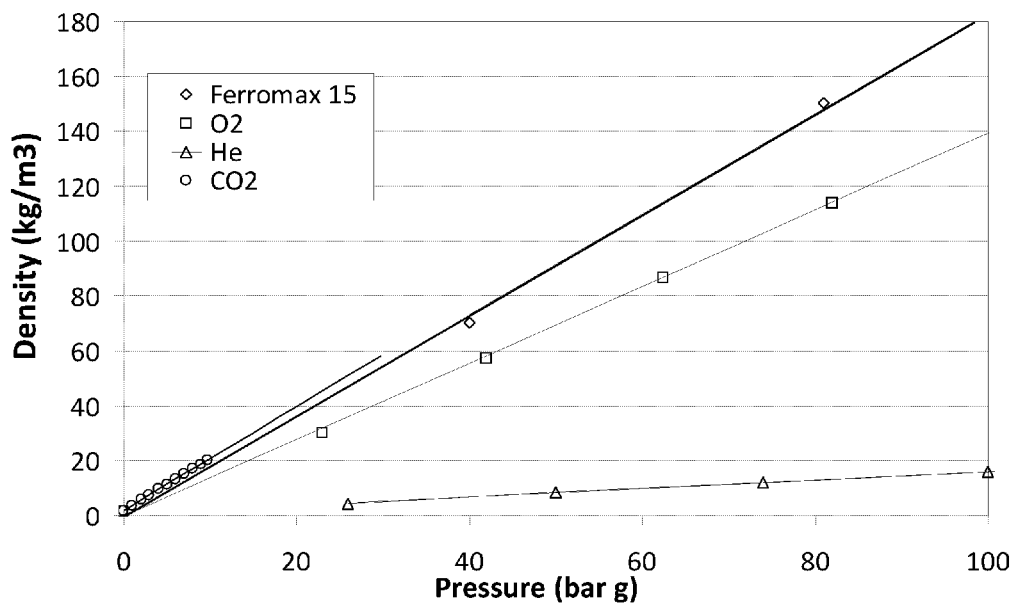
FIG. 11 shows a graph of gas density (in kg/m$^3$) on the Y-axis as a function of pressure (bar g) on the X-axis for Argon, Oxygen and an Argon:Carbon Dioxide:Oxygen mixture at pressures up to 100 bar g.

FIGS. 10 and 11 illustrate experimental data of molecular weight measurement. Both graphs show density (in kg/m$^3$) on the Y-axis as a function of pressure (in bar g) on the X-axis for the same four gases. The two graphs are identical save that FIG. 10 shows pressures up to 300 bar g whereas FIG. 11 only shows pressures up to 100 bar g.

The four gases used are Ferromax 15 (an Argon:Carbon Dioxide:Oxygen mixture), Helium, Carbon dioxide and Oxygen as shown in FIG. 9. The gradient of the line is proportional to the Molecular Weight (assuming RT is constant for all three) Consequently, the quartz crystal oscillator 210 can readily determine the molecular weight of the gas or mixture of gases.

Further, the high accuracy of the quartz crystal oscillator 210 enables measurement to a very high accuracy with a resolution of parts per million. Coupled with the linear response of the quartz density sensor 202 at high densities and pressures, the high accuracy enables the molecular weight of very light gases such as H$_2$ and He to be measured accurately.

Figure 12:
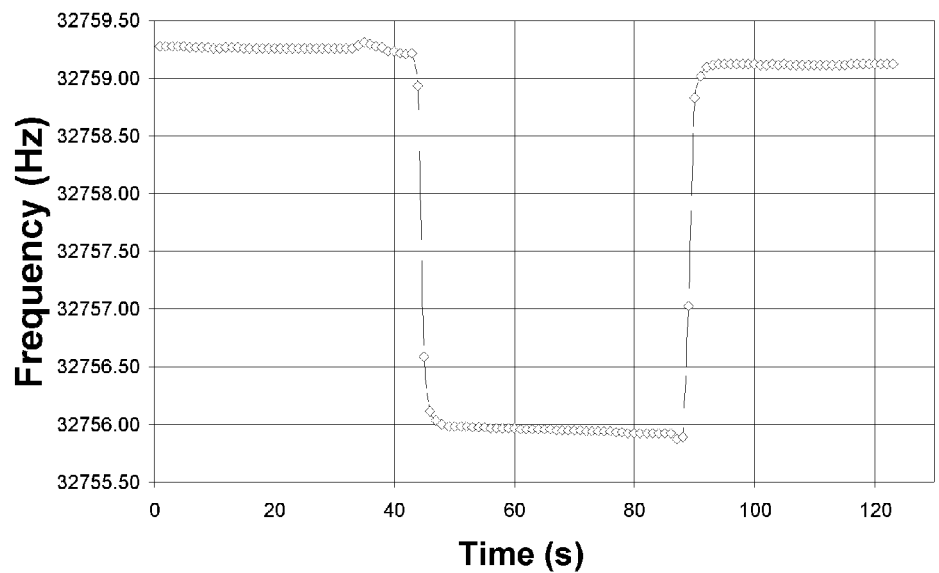
FIG. 12 is a graph showing the frequency change (in Hz) on the Y-axis as a function of time (in seconds) on the X-axis when gases are purged.
Figure 13:
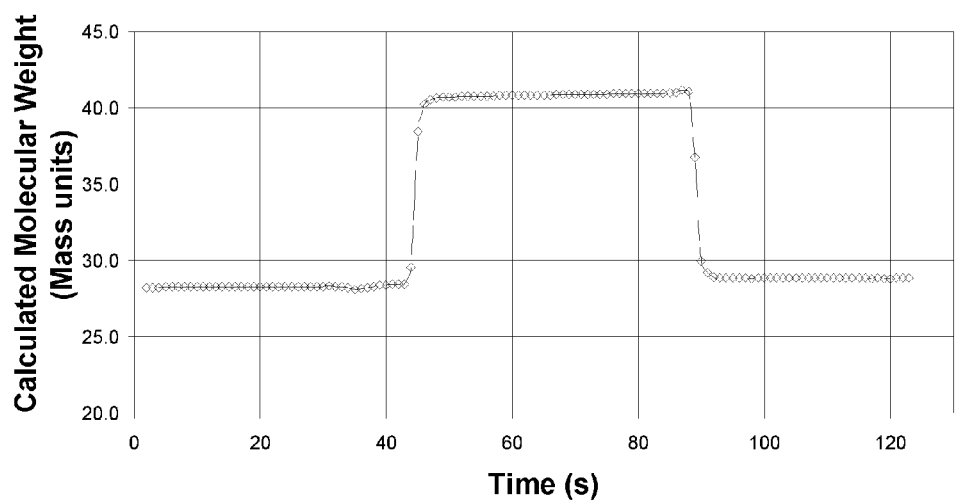
FIG. 13 is a graph corresponding to FIG. 13 showing the calculated change in molecular weight (on the Y-axis) as a function of time (in seconds) on the X-axis.

One useful application of this technology is in purge detection. FIGS. 12 and 13 illustrate experimental data of gas purge detection. Such information is vital in situations such as automatic orbital welding of pipelines.

FIG. 12 shows a graph of frequency (Hz) on the Y-axis as a function of time (in second) on the X-axis for a flow of Argon at 5 liters/minute into a Nitrogen environment, followed by refilling with Nitrogen. Clearly, the step change in frequency is readily measurable to high accuracy.

FIG. 13 shows the same data except that, in this case, the Y-axis has been calibrated to read out Molecular Weight (in Mass Units).

These figures clearly illustrate that, for most normal uses, the molecular weight of gas can be readily determined using a quartz crystal oscillator. Further, the change in molecular weight occurring when one gas is purged with another is clearly defined and identifiable. Consequently, the molecular weight change during a gas purge can be calculated with sufficient accuracy and time resolution using the quartz crystal oscillator 210 and drive circuit 204.

Figure 14:
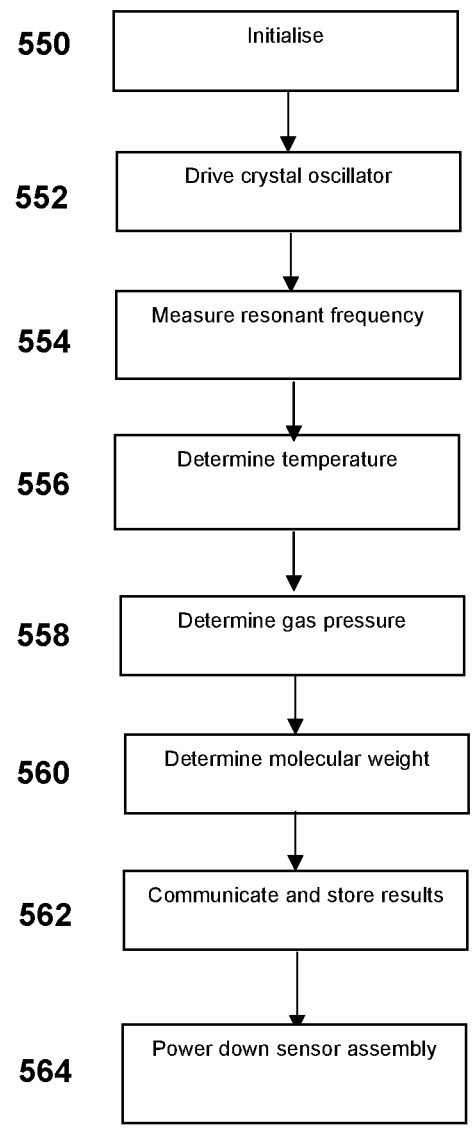
FIG. 14 is a flow chart illustrating a method according to a described embodiment.

A method according to an embodiment of the present invention will now be described with reference to FIG. 14. The method described below is applicable to each of the first to fourth embodiments described above.

Step 550: Initialise Measurement

At step 550, the measurement of the molecular weight of gas within the housing 202 is initialised. This may be activated by, for example, a user pressing a button on the outside of the housing 202. Alternatively, the measurement may be initiated by means of a remote connection, for example, a signal transmitted across a wireless network and received by the molecular weight meter 200, 300, 400, 500 through an antenna.

As a further alternative or addition, the molecular weight meter 200, 300, 400, 500 may be configured to initialise remotely or on a timer. The method proceeds to step 552.

Step 552: Drive the Quartz Crystal Oscillator

Once initialised, the drive circuit 212 is used to drive the quartz crystal oscillator 210. During initialisation, the drive circuit 212 applies a random noise AC voltage across the crystal 210. At least a portion of that random voltage will be at a suitable frequency to cause the crystal 210 to oscillate. The crystal 210 will then begin to oscillate in synchrony with that signal.

As will be appreciated, the quartz crystal oscillator 210 is, in essence, a self-contained detector and driver since the resonant frequency of the crystal itself is being measured.

By means of the piezoelectric effect, the motion of the quartz crystal oscillator 210 will then generate a voltage in the resonant frequency band of the quartz crystal oscillator 210. The drive circuit 212 then amplifies the signal generated by the quartz crystal oscillator 210, such that the signals generated in the frequency band of the quartz crystal resonator 202 dominate the output of the drive circuit 212. The narrow resonance band of the quartz crystal filters out all the unwanted frequencies and the drive circuit 212 then drives the quartz crystal oscillator 210 at the fundamental resonant frequency f. Once the quartz crystal oscillator 210 has stabilised at a particular resonant frequency, the method proceeds to step 554.

Step 554: Measure Resonant Frequency of Quartz Crystal Oscillator

The resonant frequency f is dependent upon the environmental conditions within the housing 202. In the present embodiment, the change in resonant frequency Δf is, to a good approximation, proportional in magnitude to the change in density of the gas in the interior 206 of the housing 202 and will decrease with increasing density.

In order to make a measurement, the frequency of the quartz crystal oscillator 210 is measured for a period of approximately 1 s. This is to enable the reading to stabilise and for sufficient oscillations to be counted in order to determine an accurate measurement. The measurement of frequency is carried out in the processor 230. The processor 230 may also log the time, $T_1$, when the measurement was started.

Once the frequency has been measured, the method proceeds to step 556.

Step 556: Measure Temperature of Gas

At step 556, the temperature sensor 214 measures the temperature of the gas within the housing 202. This measurement is carried out in order improve the accuracy of the calculation of the molecular weight from the frequency change measured in step 554.

The temperature measurement does not need to be particularly accurate. For example, if the temperature sensor 214 is accurate to 0.5° C., then this corresponds to an error of only approximately one part in six hundred (assuming normal atmospheric temperatures) on the absolute temperature value required for the calculation of molecular weight in later steps.

As an alternative, this step may simply involve a fixed temperature value being inputted to the processor 230. This may occur, for example, in situations where a known temperature environment is used. In this case, the temperature sensor 214 is not required.

Step 558: Determine the Pressure of Gas

Once the frequency of the quartz crystal oscillator 210 has been measured satisfactorily in step 554 and the temperature measured in step 556, the processor 230 then determines the pressure of gas within the interior 206 of the housing 202.

This may be done with an input value from the pressure sensor 302 (if provided) which provides an electrical signal proportional to the measured pressure in the housing 202. This applies for the second and fourth embodiments.

Alternatively, the pressure value may be inputted to the processor 230 manually or automatically if the pressure is known to a reasonable degree. This may correspond to the output of a fixed pressure regulator (as in the first embodiment) or may correspond to atmospheric pressure (as in the third embodiment).

Step 560: Determine the Molecular Weight of Gas

This is done using equation 8) above where the density ρ, pressure P and temperature T of the gas is known. Therefore, knowing the resonant frequency as measured in step 554, the known temperature T of the gas in the housing 202 measured in step 556 and the known pressure of the gas as determined in step 558, an accurate measurement of molecular weight (or average molecular weight for a homogenous mixture of gases) can be made. The method then proceeds to step 562.

Step 562: Communicate and Store Results

The molecular weight of the gas can be displayed in a number of ways. For example, a screen (not shown) attached to the housing 202 or regulator 150, 250 could display the molecular weight (or average molecular weight) of the gas. In the alternative, the pressure measurement could be communicated remotely to a base station or to a meter located on an adjacent fitting as will be described later.

Once the molecular weight meter 200, 300, 400, 500 for later retrieval. As a yet further alternative, pressure of gas at time $T_1$ could be stored in a memory local to said processor 230 to generate a time log.

The method then proceeds to step 564.

Step 564: Power Down Sensor Assembly

It is not necessary to keep the molecular weight meter 200, 300, 400, 500 operational at all times. To the contrary, it is beneficial to reduce power consumption by switching the molecular weight meter 200, 300, 400, 500 off when not in use. This prolongs the life of the battery 216.

The configuration of the drive circuit 212 enables the quartz crystal oscillator 210 to be restarted irrespective of the pressure in the housing 202. Therefore, the molecular weight meter 200, 300, 400, 500 can be shut down as and when required in order to save battery power.

A further application of the molecular weight meter according to the present invention is in a feedback-type gas mixer. In such an arrangement, two dissimilar gases are required to be mixed in precise concentrations and ratios. This may be required in situations such as, for example, welding applications where a mixture of Argon and Carbon Dioxide are required, with the Carbon Dioxide percentage being well defined. Further, for medical applications, the relative percentage of a particular type of gas may be required to be known to a high degree of accuracy.

Figure 15:
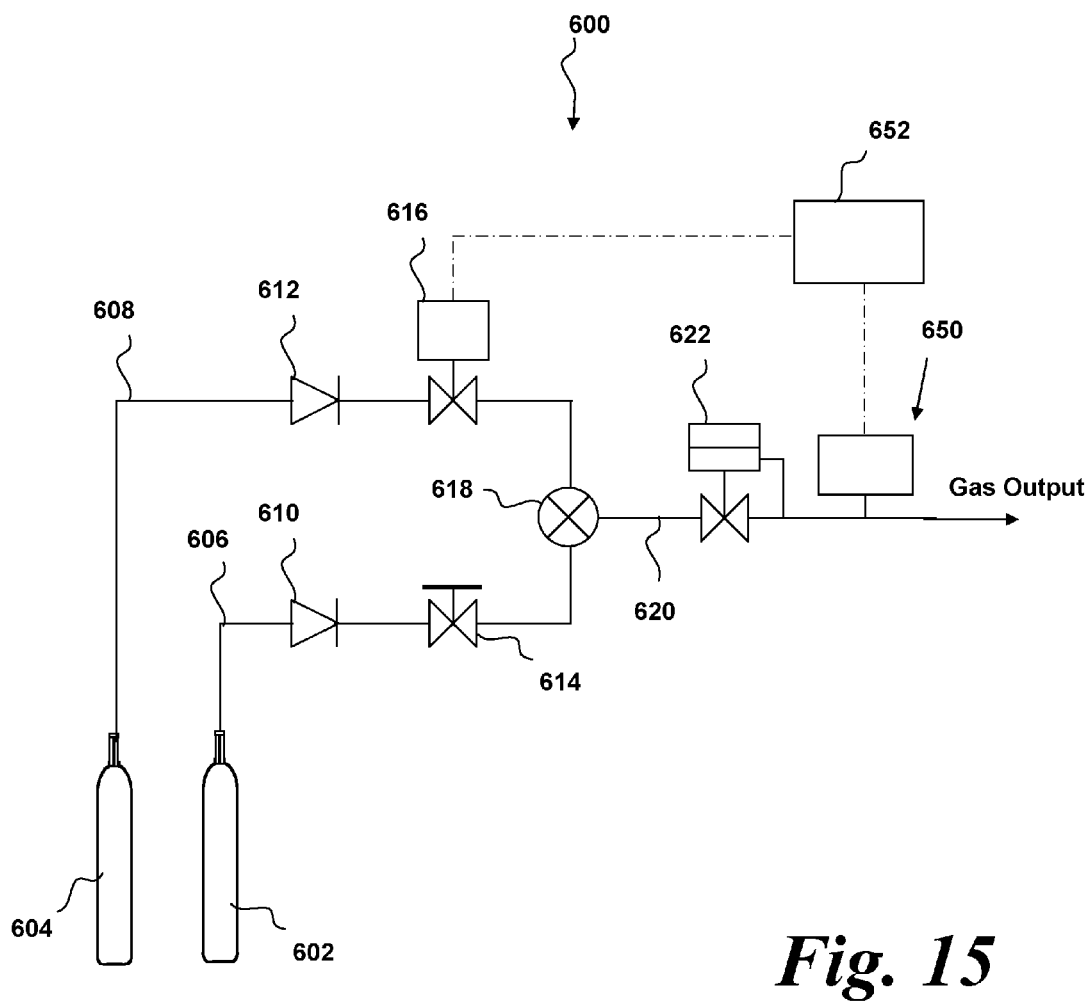
FIG. 15 shows a schematic diagram of a fifth embodiment of the present invention showing a gas mixer arrangement.

A fifth embodiment of the present invention is shown in FIG. 15. FIG. 15 shows a gas mixer 600 and a molecular weight meter 650 according to a fifth embodiment of the present invention.

The gas mixer 600 comprises a first gas source 602 and a second gas source 604. In this embodiment, the gas sources 602, 604 comprise gas cylinders which are arranged to store permanent gases under high pressure. Each cylinder comprises a valve (not shown) which may be similar to the valve 104 shown in the first embodiment.

The gases contained within each gas cylinder are dissimilar and are selected in dependence upon the required use. For example, in welding applications, a mixture of Argon and Carbon Dioxide is used. Alternatively, for medical applications, a mixture of Oxygen and Nitrogen may be required.

The first and second gas sources 602, 604 are connected to first and second supply lines 606, 608 respectively. Non-return valves 610, 612 are located in the first and second supply lines respectively downstream of the respective first and second gas sources 602, 604 to prevent back flow of gases towards the gas sources 602, 604.

Further, a main valve 614 is located in the first supply line 606 downstream of the non-return valve 610. The main valve 614 is manually operable and may take any suitable form. For example, the main valve 614 may take the form of a simple on/off valve, or may comprise an adjustable flow valve, VIPR or regulator. Alternative, the main valve 614 may be electronically controlled by a user remote from the gas mixer 600. The overall flow rate of the mixture of gases (described later) is set by the main valve 614.

A solenoid valve 616 is located in the second supply line 608 downstream of the non-return valve 612. The solenoid valve 616 comprises an armature (not shown) which is movable in response to an electric current through a set of coils (not shown) located in the body of the solenoid valve 616. The armature is movable to open or to close the solenoid valve 616 to enable gas to flow past the solenoid valve 616 to components downstream thereof.

The solenoid valve 616 may be in the normally open condition. In other words, in the absence of an electrical current through the solenoid valve 616, the armature is in a retracted position such that the solenoid valve 616 is open, i.e. gas from the second gas source 604 is able to flow therethrough to components downstream of the solenoid valve 616. If a current is applied to the solenoid valve 616, the armature will retract and the solenoid valve 616 will be closed, preventing gas from flowing therethrough. In this embodiment, the solenoid valve 616 is continuously variable in a linear direction.

The skilled person would be readily aware of the different types of solenoid valve which could be used with the present invention. For example, the armature may act directly as a selectably-operable flow restriction. Alternatively, the armature could act directly on a diaphragm. As a further alternative, the armature could control flow through a narrow conduit in communication with the supply line 608 downstream of the solenoid valve 616 in order to regulate movement of a diaphragm. Such an arrangement is known as a diaphragm pilot valve. The solenoid valve 616 is controlled by the molecular weight meter 650 as will be described later.

The first and second supply lines 606, 608 are both connected to a mixer unit 618. The mixer unit 618 is operable to combine the two flows from the first and second supply lines 606, 608 and to pass the combined flow to a third supply line 620. The mixer unit 618 merely acts to combine the two flows and does not alter the proportion of gas or pressure in each flow.

A fixed pressure regulator 622 is located in the third supply line 620 downstream of the mixer unit 618. The pressure regulator 622 is substantially similar to the fixed pressure regulator 150 described with reference to the first embodiment, and so will not be described further here. The fixed pressure regulator 622 is arranged to regulate the pressure of the gas received from the mixer unit 618 and to provide gas to portions of the third supply line 620 downstream of the fixed pressure regulator 622 at a constant pressure. This pressure may be, for example, 5 bar.

The fifth embodiment comprises a molecular weight meter 650. The components of the molecular weight meter 650 are substantially similar to those of the molecular weight meter 200 of the first embodiment and so will not be described further here. However, the molecular weight meter 650 further comprises an electronic solenoid drive 652 connected to the solenoid valve 616 and to the sensor assembly 204 of the molecular weight meter 650.

The solenoid drive 652 is arranged to receive a signal from the sensor assembly 204 and to control the solenoid valve 616 in response to that signal. Consequently, the molecular weight meter 650 is operable to control the flow of gas through the solenoid valve 616. In other words, the molecular weight meter 650 and solenoid valve 616 form a feedback loop which allows precise and remote pressure regulation of the flow of gas along the second supply line 608 to the mixer 618. Therefore, the proportion of the gases mixed in the mixer unit 618 can be controlled precisely as will be described later.

The solenoid drive 652 may comprise any suitable drive circuit for controlling the solenoid valve 616. One suitable circuit may be an operational amplifier arrangement having an input from the sensor assembly 204 to the negative terminal of the operational amplifier. Consequently, a variable resistor could be attached to the positive terminal. The variable resistor may be arranged to provide a constant reference level and act as a comparator. The reference level may be varied automatically or manually.

An input from the sensor assembly 204 to the solenoid drive 652 will cause operation of the solenoid valve 616. For example, if the input signal from the sensor assembly 204 (or, alternatively, the processor 230) exceeds a particular threshold level, the solenoid drive 652 may energise the solenoid valve 616. The solenoid valve 616 may be controlled in a digital (i.e. on or off) manner where a DC voltage is varied between a maximum and a minimum value. Alternatively, the DC voltage from the solenoid drive 652 may be continuously variable to adjust accurately the amount of flow restriction through the solenoid valve 616.

Additionally or alternatively, the solenoid drive 652 may control the solenoid valve 616 by means of a DC output comprising an AC component. Since the extension of the armature from the solenoid valve 616 is approximately proportional to the applied current, this causes the armature of the solenoid valve 616 to oscillate. Such oscillations mitigate stiction of the armature, i.e. assist in preventing the armature from becoming stuck or jammed.

Alternatively, other control arrangements, such as FETs, processors or ASICs may be used as appropriate to control the operation of the solenoid valve 616. Further, the solenoid valve 616 may operate in either a digital (i.e. on/off) or analogue (i.e. continuously variable) modes to enable accurate movement of the armature or similar.

In FIG. 15, the main components of the molecular weight meter 650 are shown separately from the solenoid valve 616. In such a situation, the solenoid valve 616 may be controlled remotely by means of wireless communication between the sensor assembly 204 and the solenoid drive 652.

Whilst the above embodiment has been described with reference to the molecular weight meter 650 and fixed pressure regulator 622, other variations may be used. For example, the fixed pressure regulator 622 may be omitted or replaced with a variable pressure regulator, such as the regulator 250 shown in FIG. 3. In this alternative, the molecular weight meter 650 will require a pressure sensor such as the pressure sensor 302 of the molecular weight meter 300 of the second embodiment.

Alternatively, the fixed pressure regulator 622 may be omitted and the molecular weight meter 650 may have a conduit to atmosphere as set out in the molecular weight meter 300 of the third embodiment. In this situation, a pressure gauge is not required as the pressure within the housing 202 of the molecular weight meter 650 will always be at atmospheric pressure.

The operation of the gas mixer 600 will now be described. As previously discussed, the molecular weight meter 650 is able to determine the molecular weight of a gas, or the average molecular weight of a gas. When two gases are mixed in different proportions, the average molecular weight of the gas mixture will vary according to the relative proportion of each gas. Therefore, by making a measurement of the average molecular weight of the mixture, and with knowledge of the molecular weights of each individual gas, the proportion of each gas in the mixture can be determined.

The main flow rate of the gas from the first gas source 602 is set by the main valve 614 which, as previously described, is user operable. Once this has been set, the molecular weight meter 650 is able to control the solenoid valve 616 to dispense the correct amount of gas from the second gas source 604 in order to achieve a desired proportional mixture of gases. This is done through the solenoid drive 652.

Therefore, if the proportion of gas from the second gas source 604 is too high, the molecular weight meter 650 will, via the solenoid drive 652, close or partially close the solenoid valve 616 to restrict the flow of gas from the second gas source 604. Concomitantly, if the proportion of gas from the second gas source 604 is too low, the molecular weight meter 650 will, via the solenoid drive 652, open or partially open the solenoid valve 616 to increase the flow of gas from the second gas source 604.

The above embodiment provides a low cost, reliable and robust method of providing a gas mixture in which the ratio of each gas in the mixture can be reliably and accurately determined and maintained.

Variations of the above embodiments will be apparent to the skilled person. The precise configuration of hardware and software components may differ and still fall within the scope of the present invention. The skilled person would be readily aware of alternative configurations which could be used.

Figure 16:
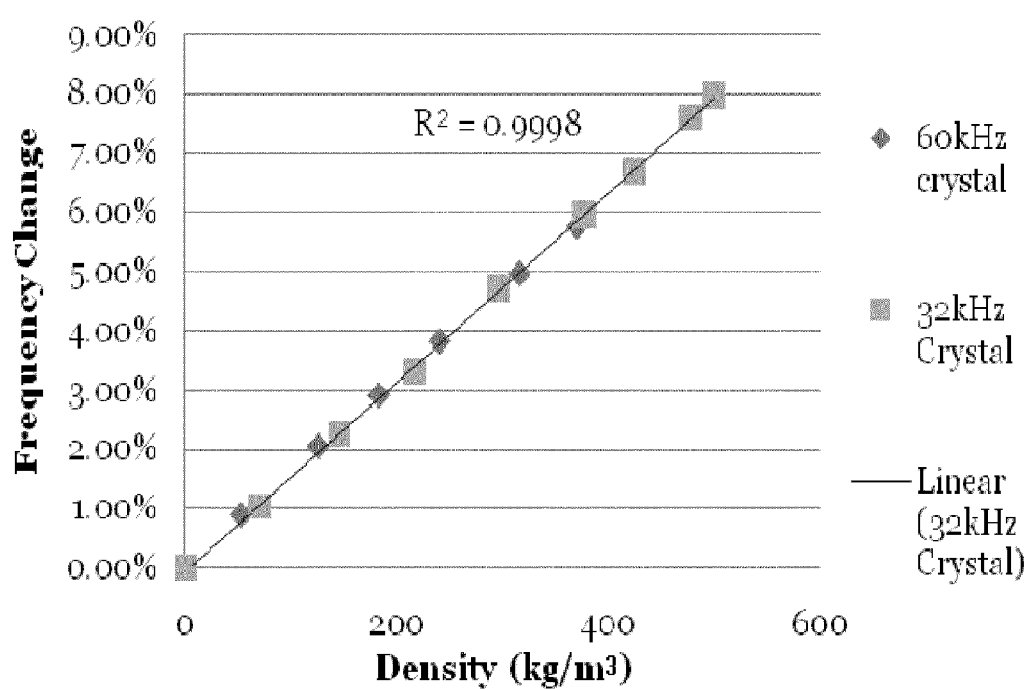
FIG. 16 shows a graph of the frequency behaviour of different crystal types.

For example, the above described embodiments have utilised a quartz crystal oscillator having a fundamental frequency of 32.768 kHz. However, crystals operating at alternative frequencies may be used. For example, quartz crystal oscillators operating at 60 kHz and 100 kHz may be used with the embodiments described above. A graph showing the frequency change with density for different crystals is shown in FIG. 16. As a further example, a crystal oscillator operating at a frequency of 1.8 MHz could be used.

Higher frequency operation enables the pressure to be monitored more frequently because a shorter time period is required to sample a given number of cycles. Additionally, higher frequency crystals enable a smaller duty cycle to be used in a "sleep" mode of a crystal. By way of explanation, in most cases, the crystal and drive circuit will spend most of the time switched off, only being switched on for a second or so when a measurement is needed. This may occur, for example, once a minute. When a higher frequency crystal is used, the pressure can be measured faster. Therefore, the time in which the crystal is operational can be reduced. This may reduce power consumption and concomitantly improve battery life.

Additionally, the above embodiments have been described by measuring the absolute frequency of a quartz crystal oscillator. However, in self-contained electronics incorporated in a gas cylinder associated regulator, it may advantageous to measure the shift in frequency of the sensor by comparing that frequency with a reference crystal of identical type but enclosed in a vacuum or pressure package. The pressure package may contain gas at a selected density, gas under atmospheric conditions or may be open to the atmosphere external of the gas cylinder.

Figure 17:
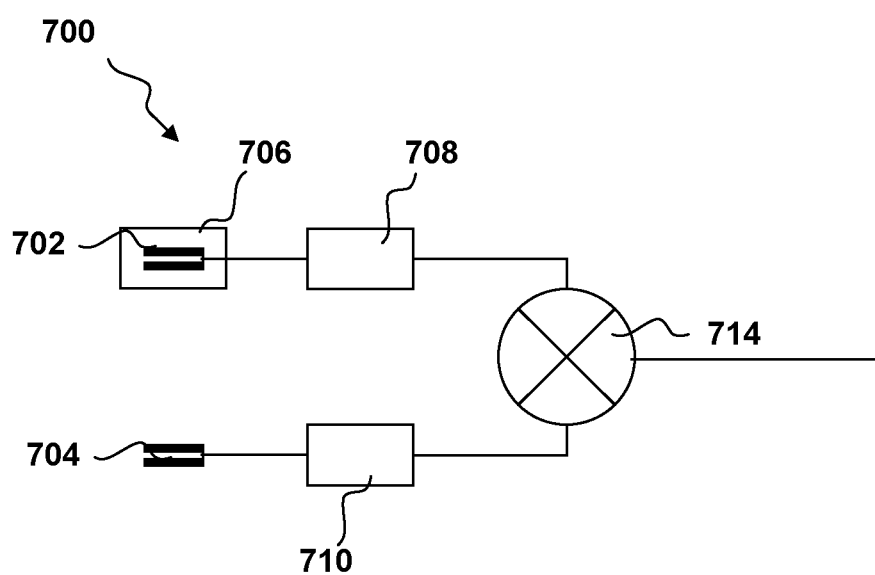
FIG. 17 is a schematic diagram showing an alternative sensor assembly comprising two quartz crystals.

A suitable sensor assembly 700 is shown in FIG. 17. The sensor assembly 700 comprises a first quartz crystal oscillator 702 and a second quartz crystal oscillator 704. The first quartz crystal oscillator 402 is a reference crystal which is located within a sealed container 706 under vacuum. The first quartz crystal oscillator 702 is driven by a drive circuit 708.

The second quartz crystal oscillator 704 is a crystal similar to the crystal 210 described in the earlier embodiments. The second quartz crystal oscillator 704 is exposed to the gas environment within the housing 202. The second quartz crystal oscillator 704 is driven by a drive circuit 710.

This comparison may be performed using an electronic mixer circuit 714 which combines the two frequency signal and produces an output at a frequency equal to the difference between the two crystals. This arrangement enables small changes due to, for example, temperature to be negated.

Further, the circuitry used in the sensor assembly 204 can be simplified because only the difference frequency is required to be measured. Further, this approach is particularly suitable for use with a high frequency (MHz) crystal oscillator, where it may be difficult to measure the crystal frequency directly.

Additionally, all of the electronics required to measure and display the density, mass or mass flow need not be mounted on or in the gas cylinder. For example, electronic functions could be split between units mounted on the cylinder permanently and units mounted on either a customer's usage station or temporarily mounted on the outlet of the cylinder such as the position normally used for a conventional flow meter.

Figure 18:
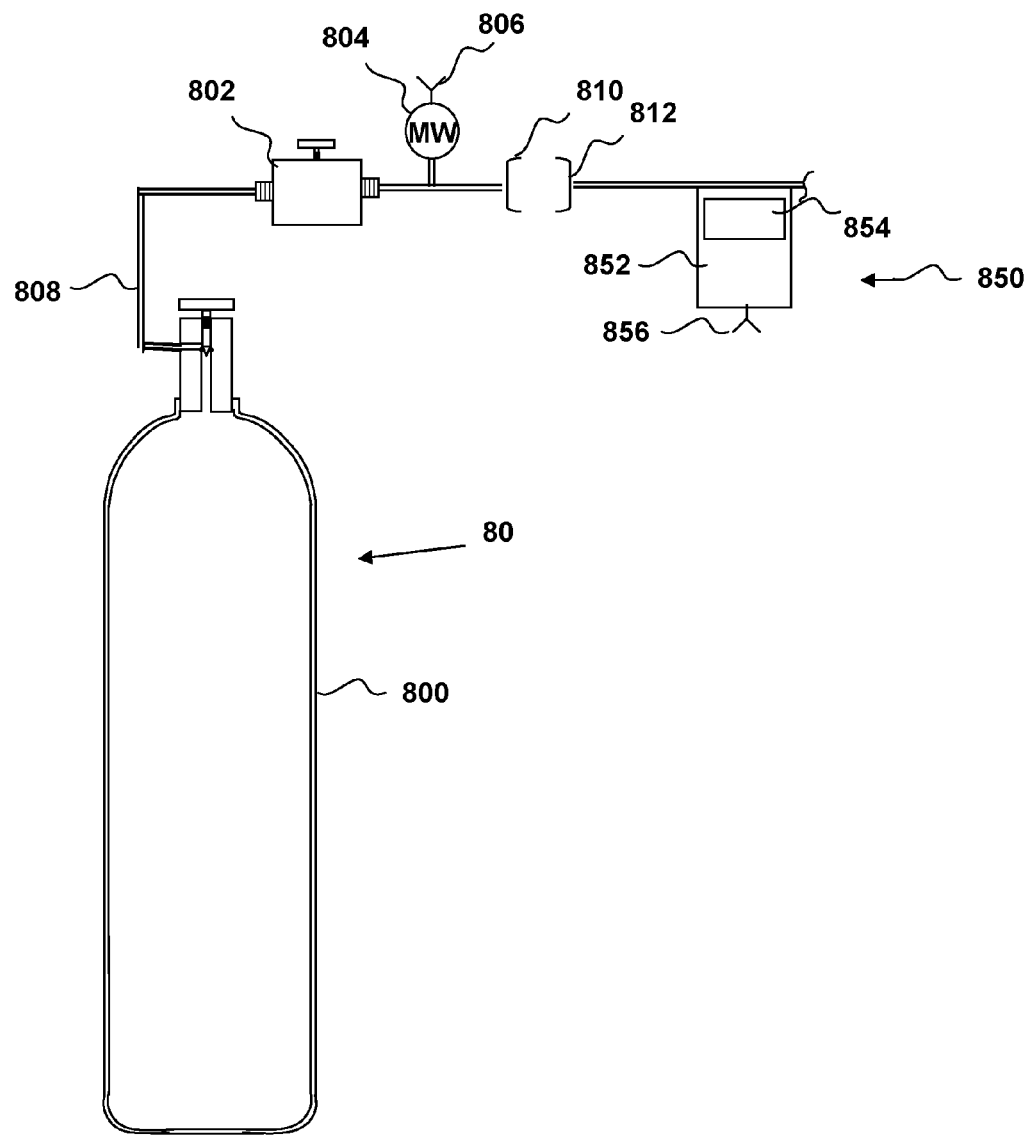
FIG. 18 shows an alternative arrangement using a remote electronic data unit.

An example of this arrangement is shown with reference to FIG. 18. The arrangement comprises a gas cylinder assembly 80 comprising a gas cylinder 800, a regulator 802 and a molecular weight meter 804. The gas cylinder 800, regulator 802 and molecular weight meter 804 are substantially similar to the gas cylinder 100, regulator 150 and molecular weight meter 200, 300, 400, 500 substantially as previously described with reference to previous embodiments.

In this embodiment, the molecular weight meter 804 comprises a quartz crystal oscillator and drive circuit (not shown) similar to the quartz crystal oscillator 210 and drive circuit 212 of earlier embodiments. An antenna 806 is provided for communication via any suitable remote communication protocol; for example, Bluetooth, Infra-red (IR) or RFID. Alternatively, one-wire communication may be utilised.

As a further alternative, acoustic communication methods may be used. The advantage of such methods is that remote communication can be effected without the requirement for an external antenna.

A connection pipe 808 is connected to the outlet of the gas cylinder 800. The connection pipe is terminated by a quick connect connection 810. The quick connect connection 810 enables connecting pipe work or components to be connected and disconnected easily and quickly from the gas cylinder 800.

A quick connect unit 850 is provided for connection to the gas cylinder 800. A complementary quick connect connector 812 is provided for connection to the connector 808. Further, the quick connect unit 850 is provided with a data unit 852. The data unit 552 comprises a display 554 and an antenna 556 for communication with the antenna 804 of the gas cylinder assembly 80. The display 554 may comprise, for example, an LCD, LED or daylight-readable display to minimise power consumption and maximise visibility of the display.

The data unit 852 may log various parameters as measured by the sensor assembly 802 of the gas cylinder assembly 80. For example, the data unit 852 could log molecular weight versus time. Such a log could be useful, for example, to welding contractors wishing to check that gas flow was present and correct during lengthy gas welding procedures on critical components, or to supply a company data on a particular customer's usage.

Additionally, the data unit 850 may be arranged to provide the following functions: to provide an audible or visible alarm if the gas type changes; to contain and display data on the type of gas; to provide multimode operation, e.g. a supplier/filler mode and a customer mode; to allow input of data; to provide data such as a cylinder number, the type of gas, a certificate of analysis, a customer history (who had the cylinder over what dates), safety data and operational tips can be carried in summary form on the cylinder.

As an alternative, all of the above examples may, optionally, be processed, stored or obtained from a system located entirely on (or within) the gas cylinder 800 or housing 202 as discussed in terms of the molecular weight meter 200, 300, 400, 500.

Whilst the above embodiments have been described with reference to the use of a quartz crystal oscillator, the skilled person would be readily aware of alternative piezoelectric materials which could also be used. For example, a non-exhaustive list may include crystal oscillators comprising: lithium tantalate, lithium niobate, lithium borate, berlinite, gallium arsenide, lithium tetraborate, aluminium phosphate, bismuth germanium oxide, polycrystalline zirconium titanate ceramics, high-alumina ceramics, silicon-zinc oxide composite, or dipotassium tartrate.

Embodiments of the present invention have been described with particular reference to the examples illustrated. While specific examples are shown in the drawings and are herein described in detail, it should be understood, however, that the drawings and detailed description are not intended to limit the invention to the particular form disclosed. It will be appreciated that variations and modifications may be made to the examples described within the scope of the present invention.

The invention claimed is:

1. A method of measuring the molecular weight of a gas, the method comprising:
   a) driving single high-frequency planar piezoelectric crystal oscillator in contact with the gas utilizing a drive circuit, such that the piezoelectric crystal oscillator resonates at a single resonant frequency despite changes in the Q factor of the piezoelectric oscillator; and
   b) measuring said single resonant frequency of said piezoelectric crystal to determine the density of gas; and
   c) determining the molecular weight of the gas from the density, a determined or pre-determined pressure of the gas, and a determined or pre-determined temperature of the gas based on a change in frequency being linearly proportional to a change in density.

2. A method according to claim 1, further comprising measuring the pressure of the gas.

3. A method according to claim 2, wherein the pressure of the gas is measured using an electronic pressure sensor.

4. A method according to claim 1, wherein the pre-determined pressure of the gas is the fixed output pressure of a gas regulator located upstream of said oscillator.

5. A method according to claim 1, wherein the pre-determined pressure of the gas is atmospheric pressure.

6. A method according to claim 1, further comprising measuring the temperature of the gas with a temperature sensor.

7. A meter for measuring the molecular weight of a gas, the meter comprising a housing having an inlet and an interior for receiving said gas to be measured, a sensor assembly comprising a single high-frequency planar piezoelectric crystal oscillator located within said housing so that, in use, the single piezoelectric crystal oscillator is in contact with said gas, said sensor assembly being arranged:
   to drive the piezoelectric crystal oscillator such that the piezoelectric crystal oscillator resonates at a single resonant frequency despite changes in the Q factor of the piezoelectric oscillator;
   to measure said single resonant frequency of said piezoelectric crystal oscillator to determine the density of gas; and
   to determine from the density, a determined or pre-determined pressure of the gas, and a determined or pre-determined temperature of the gas based on a change in frequency being linearly proportional to a change in density, the molecular weight of the gas.

8. A meter according to claim 7, wherein the sensor assembly comprises a drive circuit comprising a Darlington pair arranged in a feedback configuration from a common emitter amplifier.

9. A meter according to claim 7, further comprising a pressure sensor for measuring the pressure of the gas.

10. A meter according to claim 9, wherein said pressure sensor is an electronic pressure sensor.

11. A meter according to claim 7, wherein the meter is located downstream of a fixed pressure regulator, wherein the pressure of the gas has a predetermined value based on the output of said fixed pressure regulator.

12. A meter according to claim 7, further comprising a restricted orifice upstream of said inlet and an outlet to atmosphere downstream of said inlet, wherein said pre-determined pressure of gas is atmospheric pressure.

13. A meter according to claim 7, wherein the sensor assembly further comprises a temperature sensor.

14. A method or meter according to claim 7, wherein said piezoelectric crystal oscillator comprises at least two planar tines.

15. A meter according to claim 7, wherein said piezoelectric crystal oscillator has a resonant frequency of 32 kHz or greater.

16. A computer program product executable by a programmable processing apparatus, comprising one or more software portions for performing the steps of claim 1.

17. A computer usable storage medium having a computer program product according to claim 16 stored thereon.

18. A method according to claim 1, wherein said piezoelectric crystal oscillator comprises at least two planar tines.

19. A method according to claim 1, wherein said piezoelectric crystal oscillator has a resonant frequency of 32 kHz or greater.

* * * * *